(12) United States Patent
Lauth et al.

(10) Patent No.: US 7,723,063 B2
(45) Date of Patent: May 25, 2010

(54) METHODS FOR MEASURING LEVELS OF BIOACTIVE HUMAN HEPCIDIN

(75) Inventors: Xavier Lauth, San Diego, CA (US); Mark E. Westerman, San Diego, CA (US); Vaughn E. Ostland, La Quinta, CA (US); Jason A. Stannard, San Diego, CA (US); Michael W. Pennington, Mount Laurel, NJ (US)

(73) Assignee: Intrinsic Lifesciences, La Jolla, CA (US)

( * ) Notice: Subject to any disclaimer, the term of this patent is extended or adjusted under 35 U.S.C. 154(b) by 45 days.

(21) Appl. No.: 11/119,293

(22) Filed: Apr. 28, 2005

(65) Prior Publication Data

US 2006/0019339 A1    Jan. 26, 2006

Related U.S. Application Data

(60) Provisional application No. 60/566,387, filed on Apr. 28, 2004.

(51) Int. Cl.
| G01N 33/00 | (2006.01) |
| G01N 33/53 | (2006.01) |
| G01N 33/543 | (2006.01) |
| C07K 14/00 | (2006.01) |

(52) U.S. Cl. .................. 435/7.93; 435/7.1; 435/7.5; 436/86; 436/518; 530/324

(58) Field of Classification Search ............. None
See application file for complete search history.

(56) References Cited

U.S. PATENT DOCUMENTS

| 5,612,458 A * | 3/1997 | Hyldig-Nielsen et al. ............ 530/388.21 |
| 7,083,983 B2 * | 8/2006 | Lane et al. ............ 436/501 |
| 2004/0096987 A1 * | 5/2004 | Geacintov et al. ............ 436/518 |
| 2004/0096990 A1 | 5/2004 | Geacintov et al. |

FOREIGN PATENT DOCUMENTS

EP          1 262 187 A1 * 12/2002

OTHER PUBLICATIONS

Harlow, E. and Lane, D., Antibodies: A Laboratory Manual (1988) Cold Spring Harbor Laboratory Press, Cold Spring Harbor, NY, pp. 59-60, 72-77, 557-559, 561, 578-579, and 591-592.*
Krause et al. "LEAP-1, a novel highly disulfide-bonded human peptide, exhibits antimicrobial activity" FEBS Letters 480 (2000) 147-150.*
Harlow, E. and Lane, D., Antibodies: A Laboratory Manual (1988) Cold Spring Harbor Laboratory Press, Cold Spring Harbor, NY, pp. 288-289, 292-295, 309, 340-341 and 591-592.*
Froestl "Ligands for the isolation of GABAB receptors" Neuropharmacology 38 (1999) 1641-1646.*
Pierce Applications Handbook & Catalog (2003-2004), pp. 262-264 and 341.*
Harlow, E. and Lane, D., Antibodies: A Laboratory Manual (1988) Cold Spring Harbor Laboratory Press, Cold Spring Harbor, NY, pp. 288-289, 292-295, 309, 340-341, 553, 555-559, 561, 584-589, 591-593, 599-605, and 608.*
Park et al. "Hepcidin, a urinary antimicrobial peptide synthesized in the liver" J Biol Chem. Mar. 16, 2001;276(11):7806-10. Epub Dec. 11, 2000.*
Nemeth et al. "Hepcidin, a putative mediator of anemia of inflammation, is a type II acute-phase protein" Blood. Apr. 1, 2003;101(7):2461-3. Epub Nov. 14, 2002.*
Kemna, E. et al. "Novel urine hepcidin assay by mass spectrometry" Blood. Nov. 1, 2005;106(9):3268-70.*
Brungara, C. et al. "An immunoassay for human serum hepcidin at last: Ganz klar?" Blood. Nov. 15, 2008;112(10):3922-3.*
Ganz, T. et al. "Immunoassay for human serum hepcidin" Blood. Nov. 15, 2008;112(10):4292-7.*

* cited by examiner

*Primary Examiner*—Mark L Shibuya
*Assistant Examiner*—Christine Foster
(74) *Attorney, Agent, or Firm*—Gavrilovich Dodd & Lindsey LLP; Gregory P Einhorn

(57) ABSTRACT

The present invention concerns a method for the oxidative refolding of a hepcidin polypeptide to a form that is mature, bioactive and folded as in the native configuration and molecular mass; a method for measuring the level of native, bioactive hepcidin in a vertebrate animal; a method for measuring the level of hepcidin gene expression in a vertebrate animal; and a method for regulating the production of native, bioactive hepcidin in a vertebrate animal in vivo. The present invention also concerns an antibody or fragment thereof that specifically binds to a continuous, discontinuous, and/or conformational epitope of a mature and bioactive hepcidin folded as in the native configuration; and a pharmaceutical composition that includes the antibody or a hepcidin polypeptide and that provides antimicrobial, agonistic, or antagonistic activities in vivo in a vertebrate animal.

16 Claims, 15 Drawing Sheets

SEQUENCE LISTING

```
<160> NUMBER OF SEQ ID NOS: 34

<210> SEQ ID NO 1
<211> LENGTH: 24
<212> TYPE: DNA
<213> ORGANISM: Morone chrysops

<400> SEQUENCE: 1
gagatgccag tggaatcgtg gaag                                      24

<210> SEQ ID NO 2
<211> LENGTH: 23
<212> TYPE: DNA
<213> ORGANISM: Morone chrysops

<400> SEQUENCE: 2
gaggctggag caggaatcct cag                                       23

<210> SEQ ID NO 3
<211> LENGTH: 75
<212> TYPE: DNA
<213> ORGANISM: Morone chrysops

<400> SEQUENCE: 3
ggatccgaga tgccagtgga atcgtggaag ttgctgcatt gctgtcctaa tatgagcgga    60
tgtggtgtct gctgc                                                    75

<210> SEQ ID NO 4
<211> LENGTH: 64
<212> TYPE: DNA
<213> ORGANISM: Morone chrysops

<400> SEQUENCE: 4
ggatccgagg ctggagcagg aatcctcaga acctgcagca gacaccacat ccgctcatat    60
tagg                                                                64
```

<210> SEQ ID NO 5
<211> LENGTH: 20
<212> TYPE: DNA
<213> ORGANISM: Morone chrysops

<400> SEQUENCE: 5
gttcgattcc ggagagggag                                                    20

<210> SEQ ID NO 6
<211> LENGTH: 21
<212> TYPE: DNA
<213> ORGANISM: Morone chrysops

<400> SEQUENCE: 6
ccttccttgg atgtggtagc c                                                  21

<210> SEQ ID NO 7
<211> LENGTH: 576
<212> TYPE: DNA
<213> ORGANISM: Morone chrysops

<400> SEQUENCE: 7
atcagacagg agaagaagtc aaaggagctg acaagagtca ccaaaagagt gaagaattg         60 aaaccttaaa gcagtcaaac cctcctaaga tgaagacatt cagtgttgca gttgcagtgg        120
ccgtcgtgct cgccttcatt tgccttcagg agagctctgc tgtcccagtc actgaggtgc        180
aagagctgga ggagccaatg agcaatgagt atcaagagat gccagtggaa tcgtggaaga        240
tgccgtataa caacagacac aagcgtcaca gcagccccgg tggctgtcgc ttttgctgca        300
attgctgtcc taatatgagc ggatgtggtg tctgctgcag gttctgagga ttcctgctcc        360
agcctgggat taacacaact actacttaaa ctttttaact caatgttaca ttttcactgt        420
actcctggtt gtaaatatct gaggatgtta ctggagttca tggttgctca gtaatgtgat        480
tgaatcatct aaacactgtg tttaatttct gcagatttta ctgtgtattg tcataataaa        540
gttcaatttc actgaaaaaa aaaaaaaaa aaaaaa                                   576

<210> SEQ ID NO 8
<211> LENGTH: 85
<212> TYPE: PRT
<213> ORGANISM: Morone chrysops

<400> SEQUENCE: 8

Met Lys Thr Phe Ser Val Ala Val Ala Val Val Leu Ala Phe
1               5                   10                  15

Ile Cys Leu Gln Glu Ser Ser Ala Val Pro Val Thr Glu Val Gln Glu
            20                  25                  30

Leu Glu Glu Pro Met Ser Asn Glu Tyr Gln Glu Met Pro Val Glu Ser
        35                  40                  45

Trp Lys Met Pro Tyr Asn Asn Arg His Lys Arg His Ser Ser Pro Gly
    50                  55                  60

Gly Cys Arg Phe Cys Cys Asn Cys Cys Pro Asn Met Ser Gly Cys Gly
65                  70                  75                  80

Val Cys Cys Arg Phe
                85

<210> SEQ ID NO 9
<211> LENGTH: 24
<212> TYPE: PRT
<213> ORGANISM: Acanthopagrus schegelii -continued

```
<400> SEQUENCE: 9

Ser Pro Lys Asp Cys Gln Phe Cys Cys Gly Cys Cys Pro Asp Met Ser
1               5                   10                  15

Gly Cys Gly Ile Cys Cys Thr Tyr
            20

<210> SEQ ID NO 10
<211> LENGTH: 24
<212> TYPE: PRT
<213> ORGANISM: Acanthopagrus schegelii

<400> SEQUENCE: 10

Ser Pro Ala Gly Cys Arg Phe Cys Cys Gly Cys Cys Pro Asn Met Arg
1               5                   10                  15

Gly Cys Gly Val Cys Cys Arg Phe
            20

<210> SEQ ID NO 11
<211> LENGTH: 22
<212> TYPE: PRT
<213> ORGANISM: Acanthopagrus schegelii

<400> SEQUENCE: 11

Arg Arg Cys Arg Phe Cys Cys Gly Cys Cys Pro Asp Met Ile Gly Ser
1               5                   10                  15

Gly Thr Cys Cys Lys Phe
            20

<210> SEQ ID NO 12
<211> LENGTH: 24
<212> TYPE: PRT
<213> ORGANISM: Acanthopagrus schegelii

<400> SEQUENCE: 12

Ser Pro Lys Asp Cys Gln Phe Cys Cys Gly Cys Cys Pro Asp Met Ser
1               5                   10                  15

Gly Cys Gly Ile Cys Cys Arg Phe
            20

<210> SEQ ID NO 13
<211> LENGTH: 22
<212> TYPE: PRT
<213> ORGANISM: Acanthopagrus schegelii

<400> SEQUENCE: 13

Ala Ile Lys Cys Lys Phe Cys Cys Gly Cys Cys Ile Pro Gly Val Cys
1               5                   10                  15

Gly Leu Cys Cys Arg Phe
            20

<210> SEQ ID NO 14
<211> LENGTH: 22
<212> TYPE: PRT
<213> ORGANISM: Acanthopagrus schegelii

<400> SEQUENCE: 14

Trp Arg Cys Arg Phe Cys Cys Arg Cys Cys Pro Arg Met Arg Gly Cys
1               5                   10                  15

Gly Leu Cys Cys Arg Phe
            20
```

<210> SEQ ID NO 15
<211> LENGTH: 21
<212> TYPE: PRT
<213> ORGANISM: Acanthopagrus schegelii

<400> SEQUENCE: 15

Arg Cys Lys Phe Cys Cys Arg Cys Cys Pro Asn Met Ile Gly Gly Gly
1               5                   10                  15

Thr Cys Cys Lys Phe
            20

<210> SEQ ID NO 16
<211> LENGTH: 25
<212> TYPE: PRT
<213> ORGANISM: Danio rerio

<400> SEQUENCE: 16

Gln Ser His Leu Ser Leu Cys Arg Phe Cys Cys Lys Cys Cys Arg Asn
1               5                   10                  15

Lys Gly Cys Gly Tyr Cys Cys Lys Phe
            20                  25

<210> SEQ ID NO 17
<211> LENGTH: 25
<212> TYPE: PRT
<213> ORGANISM: Fundulus

<400> SEQUENCE: 17

Gln Ser His Leu Ser Leu Cys Arg Tyr Cys Cys Lys Cys Cys Lys Asn
1               5                   10                  15

Lys Gly Cys Gly Phe Cys Cys Arg Phe
            20                  25

<210> SEQ ID NO 18
<211> LENGTH: 22
<212> TYPE: PRT
<213> ORGANISM: Lateolabrax japonicus

<400> SEQUENCE: 18

Ala Ile Lys Cys Lys Phe Cys Cys Gly Cys Cys Thr Pro Gly Val Cys
1               5                   10                  15

Gly Val Cys Cys Arg Phe
            20

<210> SEQ ID NO 19
<211> LENGTH: 21
<212> TYPE: PRT
<213> ORGANISM: Morone chrysops

<400> SEQUENCE: 19

Gly Cys Arg Phe Cys Cys Asn Cys Cys Pro Asn Met Ser Gly Cys Gly
1               5                   10                  15

Val Cys Cys Arg Phe
            20

<210> SEQ ID NO 20
<211> LENGTH: 22
<212> TYPE: PRT
<213> ORGANISM: Oreochromis niloticus

<400> SEQUENCE: 20

Gly Ile Lys Cys Arg Phe Cys Cys Gly Cys Cys Thr Pro Gly Ile Cys
1               5                   10                  15

```
Gly Val Cys Cys Arg Phe
            20

<210> SEQ ID NO 21
<211> LENGTH: 23
<212> TYPE: PRT
<213> ORGANISM: Pagrus major

<400> SEQUENCE: 21

Trp Arg Cys Arg Phe Cys Cys Arg Cys Cys Pro Arg Met Arg Gly Cys
1               5                   10                  15

Gly Leu Cys Cys Gln Arg Arg
            20

<210> SEQ ID NO 22
<211> LENGTH: 24
<212> TYPE: PRT
<213> ORGANISM: Salmo salar

<400> SEQUENCE: 22

Thr Asn Phe Pro Ile Cys Leu Phe Cys Cys Lys Cys Cys Lys Asn Ser
1               5                   10                  15

Ser Cys Gly Leu Cys Cys Ile Thr
            20

<210> SEQ ID NO 23
<211> LENGTH: 22
<212> TYPE: PRT
<213> ORGANISM: Scophthalmus maximus

<400> SEQUENCE: 23

Gly Met Lys Cys Lys Phe Cys Cys Asn Cys Cys Asn Leu Asn Gly Cys
1               5                   10                  15

Gly Val Cys Cys Arg Phe
            20

<210> SEQ ID NO 24
<211> LENGTH: 26
<212> TYPE: PRT
<213> ORGANISM: Scophthalmus maximus

<400> SEQUENCE: 24

Gln Ser His Ile Ser Leu Cys Arg Trp Cys Cys Asn Cys Cys Lys Ala
1               5                   10                  15

Asn Lys Gly Cys Gly Phe Cys Cys Lys Phe
            20                  25

<210> SEQ ID NO 25
<211> LENGTH: 22
<212> TYPE: PRT
<213> ORGANISM: Scophthalmus maximus

<400> SEQUENCE: 25

Ala Ile Lys Cys Lys Phe Cys Cys Gly Cys Cys Thr Pro Gly Val Cys
1               5                   10                  15

Gly Val Cys Cys Arg Phe
            20

<210> SEQ ID NO 26
<211> LENGTH: 26
<212> TYPE: PRT
<213> ORGANISM: Tetraodon nigrovirdis
```

```
<400> SEQUENCE: 26

Gln Ser His Leu His Leu Cys Thr Leu Cys Cys Asn Cys Cys Lys Gly
1               5                   10                  15

Asn Lys Gly Cys Gly Phe Cys Cys Lys Phe
            20                  25

<210> SEQ ID NO 27
<211> LENGTH: 25
<212> TYPE: PRT
<213> ORGANISM: Canis familiaris

<400> SEQUENCE: 27

Asp Thr His Phe Pro Ile Cys Ile Phe Cys Cys Gly Cys Cys Lys Thr
1               5                   10                  15

Pro Lys Cys Gly Leu Cys Cys Lys Thr
            20                  25

<210> SEQ ID NO 28
<211> LENGTH: 25
<212> TYPE: PRT
<213> ORGANISM: Homo sapiens

<400> SEQUENCE: 28

Asp Thr His Phe Pro Ile Cys Ile Phe Cys Cys Gly Cys Cys His Arg
1               5                   10                  15

Ser Lys Cys Gly Met Cys Cys Lys Thr
            20                  25

<210> SEQ ID NO 29
<211> LENGTH: 25
<212> TYPE: PRT
<213> ORGANISM: Mus musculus

<400> SEQUENCE: 29

Asp Thr Asn Phe Pro Ile Cys Ile Phe Cys Cys Lys Cys Cys Asn Asn
1               5                   10                  15

Ser Gln Cys Gly Ile Cys Cys Lys Thr
            20                  25

<210> SEQ ID NO 30
<211> LENGTH: 25
<212> TYPE: PRT
<213> ORGANISM: Mus musculus

<400> SEQUENCE: 30

Asp Ile Asn Phe Pro Ile Cys Arg Phe Cys Cys Gln Cys Cys Asn Lys
1               5                   10                  15

Pro Ser Cys Gly Ile Cys Cys Glu Glu
            20                  25

<210> SEQ ID NO 31
<211> LENGTH: 25
<212> TYPE: PRT
<213> ORGANISM: Pan troglodytes

<400> SEQUENCE: 31

Asp Thr His Phe Pro Ile Cys Ile Phe Cys Cys Gly Cys Cys His Arg
1               5                   10                  15

Ser Lys Cys Gly Met Cys Cys Lys Thr
            20                  25
```

```
<210> SEQ ID NO 32
<211> LENGTH: 25
<212> TYPE: PRT
<213> ORGANISM: Pongo pygmaeus

<400> SEQUENCE: 32

Asp Thr His Phe Pro Ile Tyr Ile Phe Cys Cys Gly Cys Cys His Arg
1               5                   10                  15

Ser Lys Cys Gly Met Cys Cys Lys Thr
            20                  25

<210> SEQ ID NO 33
<211> LENGTH: 25
<212> TYPE: PRT
<213> ORGANISM: Rattus norvegicus

<400> SEQUENCE: 33

Asp Thr Asn Phe Pro Ile Cys Leu Phe Cys Cys Lys Cys Cys Lys Asn
1               5                   10                  15

Ser Ser Cys Gly Leu Cys Cys Ile Thr
            20                  25

<210> SEQ ID NO 34
<211> LENGTH: 25
<212> TYPE: PRT
<213> ORGANISM: Sus scrofa

<400> SEQUENCE: 34

Asp Thr His Phe Pro Ile Cys Ile Phe Cys Cys Gly Cys Cys Arg Lys
1               5                   10                  15

Ala Ile Cys Gly Met Cys Cys Lys Thr
            20                  25
```

METHODS FOR MEASURING LEVELS OF BIOACTIVE HUMAN HEPCIDIN

CROSS REFERENCE TO RELATED APPLICATIONS

The present patent application claims priority to Provisional Patent Application Ser. No. 60/566,387, filed on Apr. 28, 2004 and titled "Antimicrobial Peptide Isolated from Hybrid Striped Bass."

STATEMENT REGARDING FEDERALLY SPONSORED RESEARCH AND DEVELOPMENT

The research activities related to the present patent application were supported by National Science Foundation Grants DMI-0215093 and DMI-0349772.

REFERENCE TO A COMPUTER LISTING, A TABLE, OR A COMPUTER PROGRAM LISTING COMPACT DISK APPENDIX

The Sequence Listing enclosed herein is incorporated by reference.

BACKGROUND OF THE INVENTION

1. Field of the Invention

The present invention relates to a hepcidin polypeptide, and, more particularly, to a method for the oxidative refolding of a hepcidin polypeptide to a form that is mature, bioactive, and folded as in the native configuration. The present invention further relates to a method for measuring the level of hepcidin in a vertebrate animal, to a method for measuring the level of gene expression in a vertebrate animal, to a method for regulating the production of native, bioactive hepcidin a vertebrate animal in vivo, to an antibody or fragment thereof that specifically binds to an epitope of hepcidin, and to a pharmaceutical composition comprising the antibody or a hepcidin polypeptide.

2. Description of Related Art

Hepcidins form a new gene family of inducible, liver-expressed, cysteine-rich peptides that have been identified in vertebrate animals, from fish to humans.

Human hepcidin, also known as liver expressed antimicrobial peptide (LEAP-1), was initially purified as a 25 amino acid peptide from urine and plasma ultra-filtrates during screens for proteins/peptides with antimicrobial activity. Through an Advanced Technology Program Grant from the U.S. Department of Commerce to Kent Sea Tech Corp., bass hepcidin was later purified from the gill tissues of hybrid striped bass (*Morone chrysops*×*M. saxatilis*, hereinafter HSB) based on its antimicrobial activity against an *E. coli* strain, and was characterized as a second type of native, bioactive hepcidin peptide found in a vertebrate species. In vivo, bass hepcidin gene expression was shown to be strongly up-regulated following clinical infection with the pathogen *Streptococcus iniae*. The bass hepcidin peptide was shown to contain 21 amino acids like one of the forms of human hepcidin, including eight cysteines involved in four disulfide bonds, and to be predominantly expressed in the liver in the HSB model. Notably, bass hepcidin was the first hepcidin to be isolated from a non-human vertebrate, the first cysteine-rich anti-microbial peptide (AMP) isolated from fish, and the first demonstration of hepcidin gene expression induced by the bacterial infection of a vertebrate.

In addition to their antimicrobial activities, hepcidins were found to play an essential role in iron homeostasis. Such a role was first suggested in studies using subtractive cloning approaches in mice subjected to dietary iron overload, where hepcidin gene expression was up-regulated under iron-overload conditions, and where disruption of the hepcidin gene led to accumulation of iron in the liver and pancreas, as well as iron depletion in resident macrophages. This pattern closely paralleled the iron distribution pattern seen in cases of hereditary hemochromatosis in humans. In another study, over-expression of hepcidin in transgenic mouse pups induced profound anemia and postpartum mortality. These and other observations led to the hypothesis that elevated levels of hepcidin limit dietary iron uptake in duodenal enterocytes and block the release of iron by macrophages, making hepcidin a key regulator/hormone of iron homeostasis in higher vertebrates. The critical role for hepcidin in human iron regulation has recently been corroborated by the connection of deleterious mutations in the hepcidin gene in several consanguine families with severe juvenile hemochromatosis and with the demonstration of abnormal hepcidin gene expression levels in patients with other genetic variants of this disease.

The association of hepcidin with innate immune response derives from the observation of a robust upregulation of hepcidin gene expression after inflammatory stimuli, such as infections, which induce the acute phase response of the innate immune systems of vertebrates. In bass, experimental infection with the Gram-positive bacterial pathogen, *Streptococcus iniae*, strongly upregulated hepcidin gene expression within 24 hours post infection, and, in mice, hepcidin gene expression was shown to be upregulated by lipopolysaccharide (LPS), turpentine, Freund's complete adjuvant, and adenoviral infections.

Studies conducted with human primary hepatocytes indicated that hepcidin gene expression responded to the addition of interleukin-6 (IL-6), but not to interleukin-1α (IL-α) or tumor necrosis factor-α (TNF-α). Concordant with this observation, infusion of human volunteers with IL-6 caused the rapid increase of bioactive hepcidin peptide levels in serum and urine, and was paralleled by a decrease in serum iron and transferrin saturation. A strong correlation between hepcidin expression and anemia of inflammation was also found in patients with chronic and inflammatory diseases, including bacterial, fungal, and viral infections. These findings, further corroborated in a mouse model, led to the conclusion that induction of hepcidin during inflammation depends on IL-6, and that the hepcidin-IL-6 axis is responsible for the hypoferremic response and subsequent restriction of iron from blood-borne pathogens.

Evidence of the essential role of hepcidin in iron homeostasis and hypoferremia of inflammation has been primarily gathered from genetic studies in humans and mice, because only two native hepcidin peptides have been purified and the respective genes cloned and characterized to date, one from humans and the other from bass. The structure of mature, bioactive, folded, human hepcidin shows it to be an amphipathic molecule composed of two distorted, anti-parallel β-sheets separated by a hairpin loop containing a vicinal disulfide bond (that is, a disulfide bond between adjacent cysteines) and stabilized by three inter-β-sheet disulfide bonds. The distinctive structure of human hepcidin is due to a disulfide bonding pattern that appears to be highly conserved evolutionarily, and to be required for bioactivity as an iron regulatory molecule and as an antimicrobial compound.

To date, the unique structure of the mature, folded, bioactive hepcidin has severely limited the development and application of sensitive, informative, immunoglobulin antibodies and tools to detect a refolded, synthetic hepcidin and partial, linear amino acid sequences by means of methods adapted from the production of single chain antibodies. These failures suggest that antibodies that recognize discontinuous and conformational epitopes of the mature, correctly folded, bioactive hepcidin molecule of interest are required for the sensitive measurement of the bioactive forms of hepcidin in studies of disease.

The central role of hepcidin and its key functions in iron regulation and in the innate immune response to infection necessitates the invention of novel methods and informative diagnostic tools for the measurement of the mature, bioactive forms of hepcidin in vertebrates, for the regulation of hepcidin production in animals, and for the production of a synthetic hepcidin that has a properly folded tertiary structure as in the native configuration. Further, the production, refolding, purification, and validation of synthetic or recombinant hepcidin peptides, and the development of antibodies specific to the native, bioactive, vertebrate forms, will enable the treatment of human and animal diseases and infections.

BRIEF SUMMARY OF THE INVENTION

It is an advantage of the present invention to provide methods for the production of bioactive hepcidin by refolding linear hepcidin that is made available by a variety of processes, such as chemical synthesis, production in bacteria, production in yeast, and production in eukaryotic cell lines.

It is another advantage of the present invention to provide methods for determining the concentration of hepcidin in vertebrates using an Enzyme-Linked Immunosorbent Assay (ELISA) with an anti-hepcidin antibody and with a hepcidin conjugate, or using an immuno-chromatographic assay with an anti-hepcidin antibody and a hepcidin conjugate.

It is a further advantage of the present invention to provide methods for determining hepcidin gene abundance in a vertebrate animal by performing a Reverse Polymerase-Transcriptase Chain Reaction (RT-PCR) on the ribonucleic acid (RNA) present in a sample of tissue or bodily fluid of the animal.

It is yet another advantage of the present invention to provide methods for inducing production of hepcidin in vivo in vertebrate animals, thereby enhancing innate immunity.

It is still another advantage of the present invention to provide an antibody capable of binding to an epitope of hepcidin, and to further provide a diagnostic tool based on said antibody for measuring the level of hepcidin in a vertebrate animal.

It is a still further advantage of the present invention to provide a pharmaceutical composition that comprises a hepcidin polypeptide and that has antimicrobial, agonistic or antagonistic activity in relation to hepcidin bioactivity in vivo in a vertebrate animal.

Briefly, the present invention concerns a method for the oxidative refolding of a hepcidin polypeptide to a form that is mature, bioactive and folded as in the native configuration and molecular mass; a method for measuring the level of native, bioactive hepcidin in a vertebrate animal; a method for measuring the level of hepcidin gene expression in a vertebrate animal; and a method for regulating the production of native, bioactive hepcidin in a vertebrate animal in vivo. The present invention also concerns an antibody or fragment thereof that specifically binds to a continuous, discontinuous, and/or conformational epitope of a mature and bioactive hepcidin folded as in the native configuration; and a pharmaceutical composition that includes the antibody or a hepcidin polypeptide and that provides antimicrobial, agonistic, or antagonistic activities in vivo in a vertebrate animal.

A first method is provided for the oxidative refolding of a hepcidin polypeptide to a form that is mature, bioactive and folded as in the native configuration and molecular mass. This first method comprises the steps of solubilizing the hepcidin polypeptide in an acetic acid solution to produce a first solution; of diluting the first solution with an aqueous buffer solution containing a chaotropic reagent, an organic alcohol, and an oxidizing reagent to produce a second solution, in which the organic alcohol enhances the solubility of the polypeptide and prevents hepcidin precipitation during the oxidative refolding, increasing yield as a consequence; of adjusting the pH of the second solution to a level between approximately 5 and 7; and of exposing the hepcidin peptide to oxidation for a suitable period of time, which causes the polypeptide to configure to a bioactive hepcidin molecule that has a folded tertiary structure as in the native configuration.

A second method is also provided for the measurement in a vertebrate animal of the level of the hepcidin that is mature, bioactive, and folded as in the native configuration. This second method comprises the steps of obtaining a sample of tissue or bodily fluid from the animal; of causing the sample to contact an antibody or a fragment thereof; and of determining the hepcidin level in the sample. In this second method, the antibody or the fragment thereof may specifically bind to a continuous, discontinuous, or conformational epitope of the hepcidin, and the hepcidin level may be determined quantitatively, semi-qualitatively, or qualitatively.

A third method is further provided for measuring the level of hepcidin gene expression in a vertebrate animal. This third method comprises the steps of obtaining a sample of tissue or bodily fluid from the animal; of isolating the RNA of the sample; and of performing a RT-PCR on said RNA to determine hepcidin gene abundance. In this third method, the level of hepcidin gene abundance correlates with the level of a mature, folded, and bioactive form of a hepcidin peptide in the sample.

Still further, a fourth method is provided for regulating the production of native, bioactive hepcidin in a vertebrate animal in vivo. This fourth method causes an enhancement of the innate immunity of the vertebrate animal and also causes a short term protection of the vertebrate animal from infection. This fourth method comprises the step of causing an intake by the animal of one or more compounds that stimulate hepcidin gene expression and the subsequent production by the animal of the mature, folded, and bioactive hepcidin peptide.

The present invention also concerns an antibody or fragment thereof that specifically binds to a continuous, discontinuous, and/or conformational epitope of hepcidin, which hepcidin is in a form that is mature, bioactive, and folded as in the native configuration. The antibody or the fragment thereof may be affixed on a support, and may include a tracer that is capable of binding to the antibody or to the fragment thereof.

The present invention further concerns a pharmaceutical composition that includes the antibody or a hepcidin polypeptide. In this pharmaceutical composition, the hepcidin polypeptide provides properties that are antimicrobial, agonistic, or antagonistic in relation to hepcidin bioactivity in vivo in a vertebrate animal.

BRIEF DESCRIPTION OF THE FIGURES

FIG. 1 contains the following sequences: SEQ ID NO:7, or atcagacagg agaagaagtc aaaggagctg acaagagtca ccaaaagagt gaaagaattg aaaccttaaa gcagtcaaac cctcctaaga tgaagacatt cagtgttgca gttgcagtgg ccgtcgtgct cgccttcatt tgccttcagg agagctctgc tgtcccagtc actgaggtgc aagagctgga ggagccaatg agcaatgagt atcaagagat gccagtggaa tcgtggaaga tgccgtataa caacagacac aagcgtcaca gcagccccgg tggctgtcgc ttttgctgca attgctgtcc taatatgagc ggatgtggtg tctgctgcag gttctgagga ttcctgctcc agcctgggat taacacaact actacttaaa ctttttaact caatgttaca ttttcactgt actcctggtt gtaaatatct gaggatgtta ctggagttca tggttgctca gtaatgtgat tgaatcatct aaacactgtg tttaatttct gcagatttta ctgtgtattg tcataataaa gttcaatttc actgaaaaaa aaaaaaaaaa aaaaaa (shown in FIG. 1 in uppercase characters), and SEQ ID NO:8, or MKTFSVAVAV AVVLAFICLQ ESSAVPVTEV QELEEPMSNE YQEMPVESWK MPYNNRHKRH SSPGGCRFCC NCCPNMSGCG VCCRF.

FIG. 3 contains the following sequences, shown here in tabular form:
SEQ ID NO:9, or SPKDCQFCCG CCPDMSGCGI CCTY
SEQ ID NO:10, or SPAGCRFCCG CCPNMRGCGV CCRF
SEQ ID NO:11, or RRCRFCCGCC PDMIGSGTCC KF
SEQ ID NO:12, or SPKDCQFCCG CCPDMSGCGI CCRF
SEQ ID NO:13, or AIKCKFCCGC CIPGVCGLCC RF
SEQ ID NO:14, or WRCRFCCRCC PRMRGCGLCC RE
SEQ ID NO:15, or RCKFCCRCCP NMIGGGTCCK F
SEQ ID NO:16, or QSHLSLCRFC CKCCRNKGCG YCCKF
SEQ ID NO:17, or QSHLSLCRYC CKCCKNKGCG FCCRF
SEQ ID NO:18, or AIKCKFCCGC CTPGVCGVCC RF
SEQ ID NO:19, or GCRFCCNCCP NMSGCGVCCR F
SEQ ID NO:20, or GIKCRFCCGC CTPGICGVCC RF
SEQ ID NO:21, or WRCRFCCRCC PRMRGCGLCC QRR
SEQ ID NO:22, or TNFPICLFCC KCCKNSSCGL CCIT
SEQ ID NO:23, or GMKCKFCCNC CNLNGCGVCC RF
SEQ ID NO:24, or QSHISLCRWC CNCCKANKGC GFCCKF
SEQ ID NO:25, or AIKCKFCCGC CTPGVCGVCC RF
SEQ ID NO:26, or QSHLHLCTLC CNCCKGNKGC GFCCKF
SEQ ID NO:27, or DTHFPICIFC CGCCKTPKCG LCCKT
SEQ ID NO:28, or DTHFPICIFC CGCCHRSKCG MCCKT
SEQ ID NO:29, or DTNFPICIFC CKCCNNSQCG ICCKT
SEQ ID NO:30, or DINEPICREC CQCCNKPSCG ICCEE
SEQ ID NO:31, or DTHFPICIFC CGCCHRSKCG MCCKT
SEQ ID NO:32, or DTHFPIYIFC CGCCHRSKCG MCCKT
SEQ ID NO:33, or DTNFPICLFC CKCCKNSSCG LCCIT
SEQ ID NO:34, or DTHFPICIFC CGCCRKAICG MCCKT.

FIG. 6, Panel B illustrates a co-elution of a 1:1 mixture of synthetic bass hepcidin with natural material; and FIG. 6, Panel C illustrates a MALDI-TOF mass spectrum of the synthetic bass hepcidin.

DETAILED DESCRIPTION OF THE INVENTION

Figure 1:
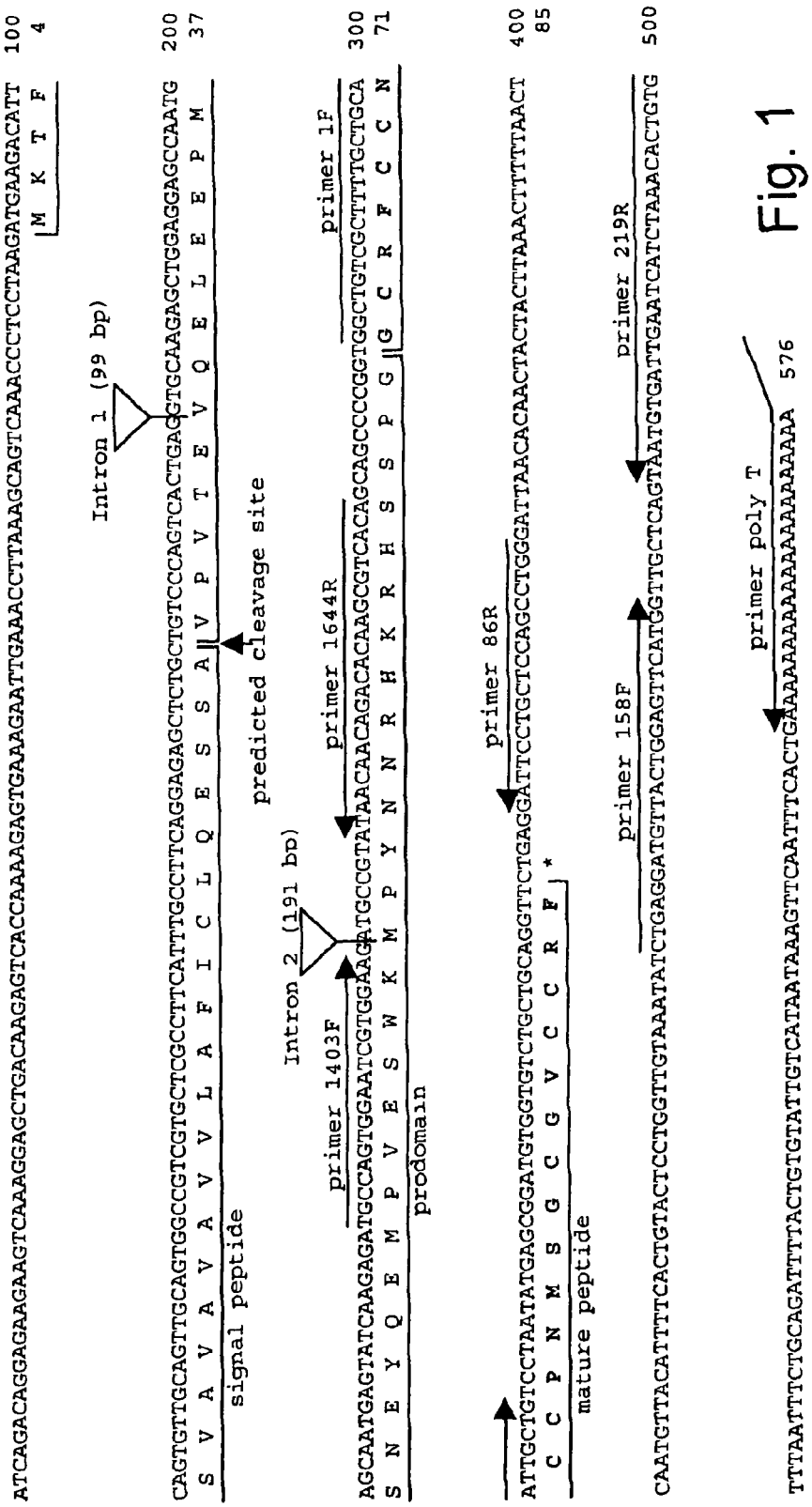
FIG. 1 shows a sequence listing illustrating the copy DNA (cDNA) and predicted amino acid sequence of white bass hepcidin, the location of introns, and the predicted peptide cleavage site, according to one aspect of the present invention.

In accordance with the present invention, there are provided novel methods for the oxidative refolding of a hepcidin polypeptide to a form that is mature, bioactive, and folded as in the native configuration; for measuring the level of hepcidin in a vertebrate animal; for measuring the level of gene expression in a vertebrate animal; and for regulating the production of native, bioactive hepcidin in a vertebrate animal in vivo.

In accordance with the present invention, there is also provided to an antibody or fragment thereof that specifically binds to an epitope of hepcidin, and a pharmaceutical composition comprising the antibody or a hepcidin polypeptide.

Small, compact peptides such as hepcidin are often difficult to raise useful antibodies against because they are generally poor immunogens. The failure of several groups of investigators to raise a useful antibody to human hepcidin led us develop novel and improved methods for development of antibodies to hepcidins. In the prior art, the unique structure of the mature, folded, bioactive hepcidin had severely limited the development and application of sensitive, informative, immunoglobulin antibodies and tools to detect refolded synthetic hepcidin and partial linear amino acid sequences using methods adapted from the production of single chain antibodies. These failures led us to believe that antibodies that recognize discontinuous and conformational epitopes of the mature, correctly folded, bioactive hepcidin molecule of interest should be required for the sensitive measurement of bioactive forms of hepcidin both in the study of diseases and of innate immunity.

The production, refolding, purification, and validation of synthetic or recombinant hepcidin peptides, and the development of antibodies specific to the native, folded, bioactive, forms of vertebrate hepcidins, will be useful by enabling sensitive diagnostics for monitoring and elucidating the role of hepcidin in human and animal diseases. Following is a description of the methodology employed to enable the present invention.

Synthesis of bass hepcidin peptide. Synthesis of one gram of the bass hepcidin peptide SEQ ID NO:19 (GCRFCCNC-CPNMSGCGVCCRF) was initiated on Fmoc-Phe-HMP resin. Side chain protected amino acid derivatives included: Fmoc-Cys(Trt)-OH, Fmoc-Ser(tBu)-OH, Fmoc-Asn(Trt) and Fmoc-Arg(Pmc)-OH. Standard Fmoc/tBu chemistry was used to assemble the primary sequence proceeding from the C-terminus to the N-terminus. Activated HOBT esters were used to mediate the coupling steps. Following primary assembly, the peptide was cleaved and simultaneously deprotected using trifluoroacetic acid (TFA): triisopropylsilane: water: thioanisole (9 ml: 0.5 ml:0.5 ml:0.5 ml) for 2 hr at RT. The spent resin beads were removed by filtration and the TFA mixture containing the crude cleaved peptide was precipitated into ice-cold diisopropyl ether. The precipitated product was recovered by filtration and washed 3 times with ice-cold ether and then subjected to amino acid analysis, C18 RP-HPLC, and mass spectroscopy to confirm successful synthesis. Amino acid analysis and mass spectroscopy results confirmed the correct number and identity of amino acids were present in the crude peptide and that the peptide had the correct mass. HPLC analysis of the crude peptide showed several minor peaks and a single major fraction that represented 33.4% of the total sample.

Figure 3:
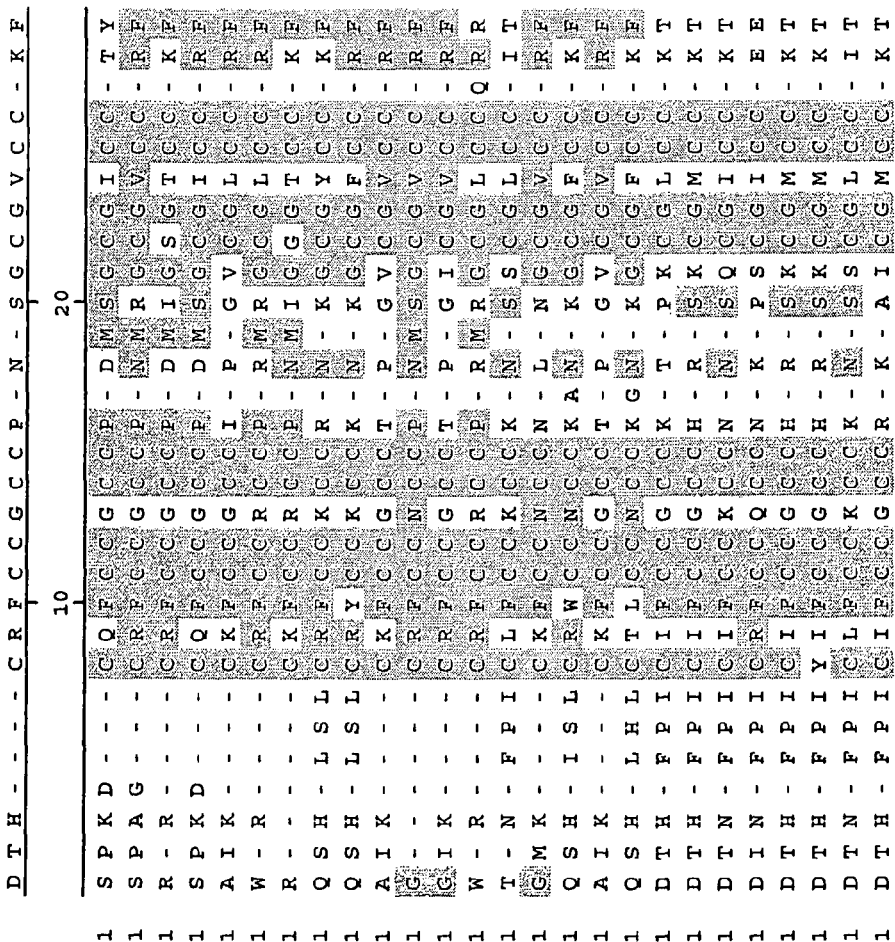
FIG. 3 is an illustration of the conserved hepcidin peptide family showing the amino acid sequence similarity of known and predicted hepcidins, more particularly, of *Morone chrysops* and *Homo sapiens* hepcidin that have been isolated and characterized from animal tissue samples, and of other sequences that are putative mature hepcidin peptide translated from cDNA sequences.

Purification of linear bass hepcidin and initial refolding experiments. We made several unsuccessful attempts to refold linear bass hepcidin using each of three different approaches that had been previously used to induce spontaneous refolding of the human hepcidin peptide in an oxidative medium. The strong similarity (60%) between bass hepcidin and human hepcidin suggested that these refolding strategies would be successful with the bass peptide. FIG. 3 is an illustration of the conserved hepcidin peptide family showing the amino acid sequence similarity of known and predicted hepcidins. In particular, *Morone chrysops* and *Homo sapiens* hepcidin are the only two peptides that have been isolated and characterized from animal tissue samples, while other sequences are putative mature hepcidin peptide translated from cDNA sequences from search of GenBank™ EST entries. Amino acids that match the *Morone chrysops* hepcidin sequence exactly are shaded. In order to enhance the probability of obtaining pure, refolded hepcidin peptide using these simple air oxidation methods, we decided to first purify linear bass hepcidin from the complex folding mixture using RP-HPLC (Phenomex C18, 250×4.6 mm, 5 μm, 120 Å, flow rate 1 ml/min, eluent A, acetonitrile (MeCN) w/0.05% trifluoroacetic acid (TFA), eluent B, water with 0.05% TFA; gradient 0-20% A over 10 min, then 20-50% A over 60 min, UV detection at 215 nm). The authentic linear hepcidin peptide eluted under these conditions at ~30% MeCN (retention time 28 min). MALDI-TOF analysis of the lyophilized fraction showed the correct molecular mass of 2263 (Mr calc. 2263.8) for bass hepcidin peptide. Using this protocol we were able to routinely purify linear bass hepcidin to very high purity for refolding experiments. The refolding protocols cited in the prior art involved simple, overnight air oxidation in phosphate buffer (pH 7.5) and water (pH 7.5), respectively, such as dialysis of human hepcidin in decreasing concentrations of guanidine hydrochloride (6 M-0 M Gun HCl) in 100 mM phosphate buffer containing 20:1 cysteine:cystine (3 mM:0.15 mM). However, none of our attempts using these published protocols yielded authentic bass hepcidin as assessed by RP-HPLC and mass spectroscopy.

In the prior art, implementation of dimethylsulfoxide-mediated oxidative refolding conditions was also unsuccessful in producing a biologically active hepcidin. Refolding in the presence of chaotropic agents and dimethylsulfoxide (DMSO) did not result in any folded product with measurable biological activity as assessed by MIC analysis of lyophilized fractions of the major peaks observed. RP-HPLC analysis of the refolding mixtures showed few if any products were produced and that those produced were in extremely low concentrations relative to the amount of input, purified, linear hepcidin. This suggested that the cationic, cysteine rich peptide was most likely aggregating and precipitating from the refolding mixture. This indicated to us that other approaches that enhanced hepcidin solubility and decreased its ability to aggregate would be required to properly fold this molecule.

Development of an improved method for refolding hepcidins. Inclusion of organic alcohols to mediate folding has been utilized in the prior art in the presence of glutathione to increase the yield of the correctly folded alpha-conotoxins. The effect of the alcohol better solubilizes the hydrophobic residues by preventing aggregation that often accompanies folding reactions. The process of folding places side chains of amino acids which are normally sequestered in an organic hydrophobic environment in direct contact with the aqueous hydrophilic environment. The organic alcohols seem to serve in co-solvent assisted manner to favor the most stable configuration. We assessed the efficacy of organic alcohols to enhance refolding of the crude, synthetic hepcidin peptide in additional refolding experiments performed with chaotropic reagents and DMSO.

Figure 4:
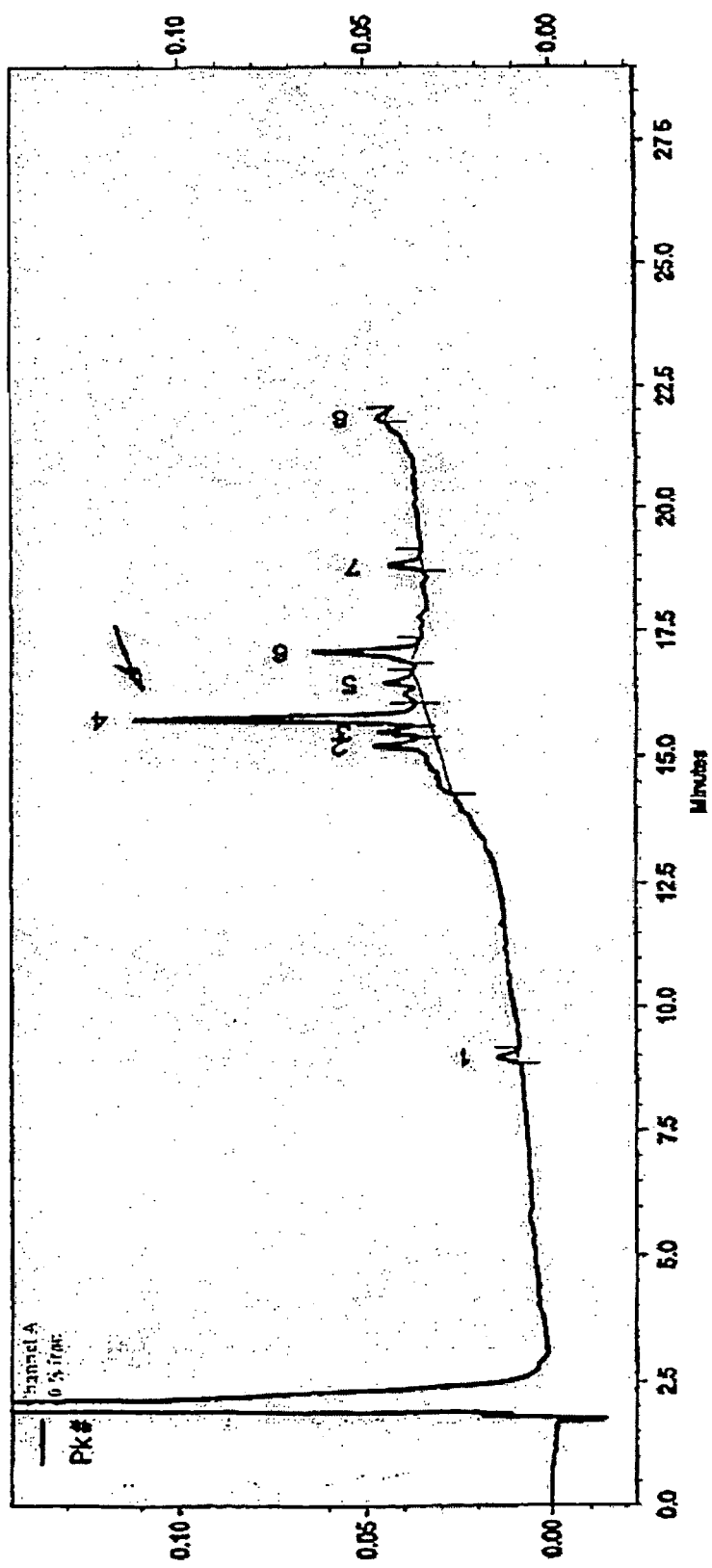
FIG. 4 illustrates the HPLC profile of a crude refolding mixture of bass hepcidin, wherein the major peaks screened by MIC are numbered 1-8.

The crude peptide was cleaved from the resin beads as described above and following the washing steps immediately dissolved in 8 M guanidinium HCl. The peptide solution was slowly diluted to a total volume of 1.5 liters in the final folding buffer (2 M guanidinium HCl, 10% DMSO, 10% isopropyl alcohol, pH 5.5) at a peptide concentration of 0.2 mg/ml. The folding mixture was left air exposed at RT and folding was complete in 18 hours. The folding mixture was then diluted with water to 2.5 liters and loaded onto RP-HPLC equipped with a Rainin DYNAMAX-ODS™ (5×30 cm) column to concentrate the sample and remove any trace organic solvents. Initial purification of bass hepcidin was performed using a two-part step gradient (15% MeCN, 0.05% TFA followed by 40% MeCN, 0.05% TFA to elute product). A HPLC profile of the crude refolding mixture eluted during the 40% MeCN step is shown in FIG. 4.

Fractions obtained from RP-HPLC analysis of peptide refolding experiments were analyzed for antimicrobial activity. Minimal inhibitory concentration (MIC) studies against a sensitive reference strain of *E. coli* were used to screen fractions (FIG. 4) derived from the refolding and HPLC purification studies. *E. coli* was shown to be extremely sensitive to a predominant HPLC fraction containing bass hepcidin (FIG. 4, peak 4; arrow; MIC of $\geq 2.7$ µM). Interestingly, two fractions (Fractions 3, 5) immediately adjacent to this fraction also contained antimicrobial activity (MIC of 22.17 µM). Mass spectroscopy analysis of these fractions showed a peak corresponding to the correct mass of bass hepcidin containing four disulfide bonds (MW 2255), indicating that they contained disulfide bond hepcidin variants (incorrectly folded hepcidin containing four disulfide bonds). The biological antimicrobial activity of these variants is a part of this invention. One skilled in the arts will appreciate that refolding variants of hepcidin can serve as agonist of antagonists of hepcidins in biological activities in vivo.

Figures 5A, 5B:
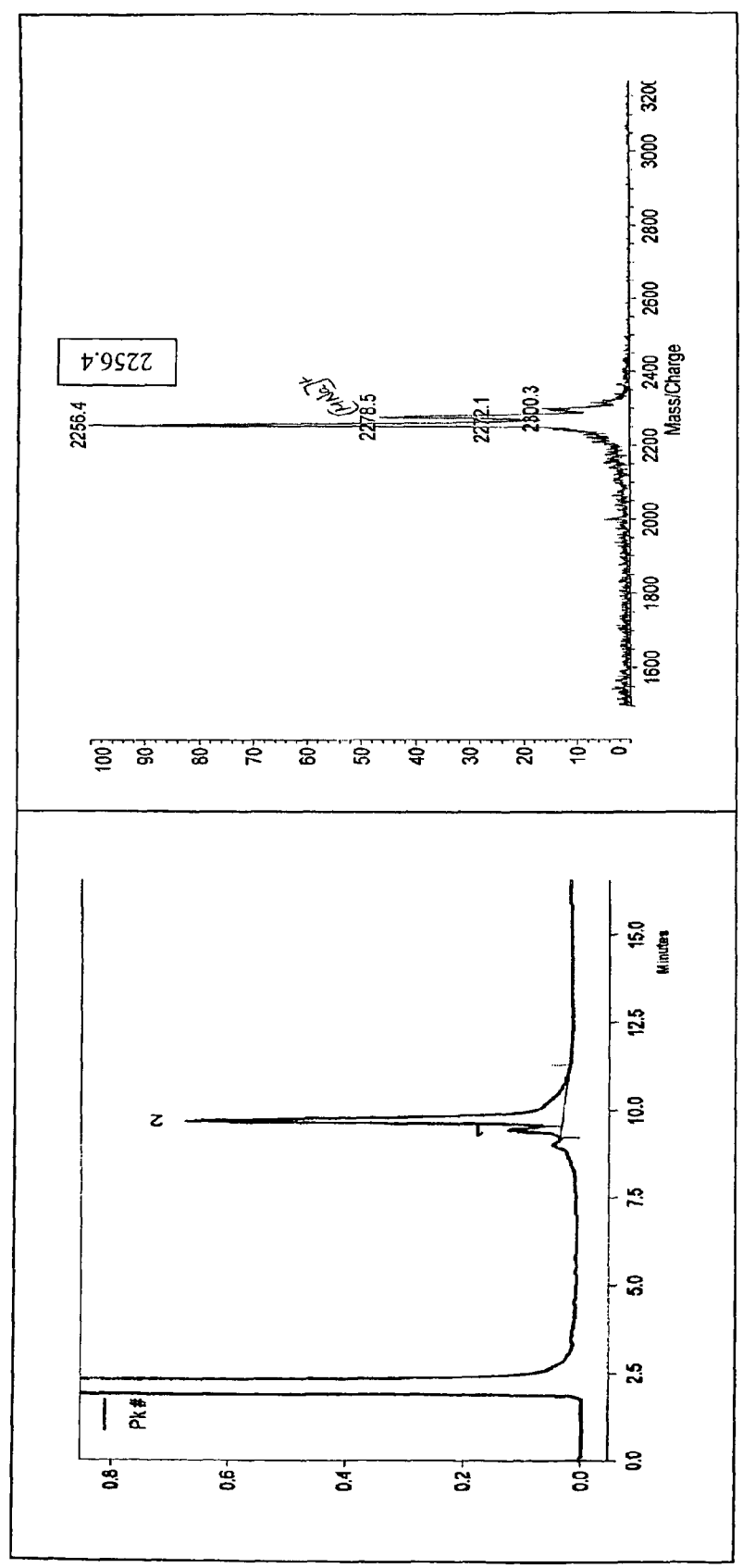
FIG. 5A shows a HPLC chromatogram of purified refolded bass hepcidin.
FIG. 5B shows a MALDI-TOF mass spectrometric analysis of bass hepcidin.

Purification of bioactive hepcidin. The material eluted with 40% MeCN was lyophilized and re-dissolved in 1:1 MeCN/H$_2$O and then diluted prior to loading to 10% MeCN. Purification was performed on a semi-preparative HPLC (Kromasil C18, 250×4.6 mm, 10 µm particle size, 120 Å pore size, flow rate 8 ml/min, eluent A, 40% MeCN, 0.1% TFA, eluent B 0.1% TFA in water; gradient was from 15 to 40% MeCN into H$_2$O containing 0.1% TFA in 100 minutes, UV detection at 215 nm). Yield of the authentic bass hepcidin from this refolding and purification protocol that began with 300 milligrams of the crude peptide was approximately 6 mg or 2% of the original cleaved product. Thus, the refolding protocol outlined above results in a reasonably robust oxidation mixture for a peptide containing 4 disulfide bonds, with the major component being the correctly refolded isomer (FIG. 4, peak 4—see arrow). In addition, we have developed a relatively simple two step protocol for HPLC purification of the correct hepcidin isomer from the complex refolding mixture shown in FIG. 4 that is relatively rapid and highly reproducible (FIG. 5A-B).

Figure 6:
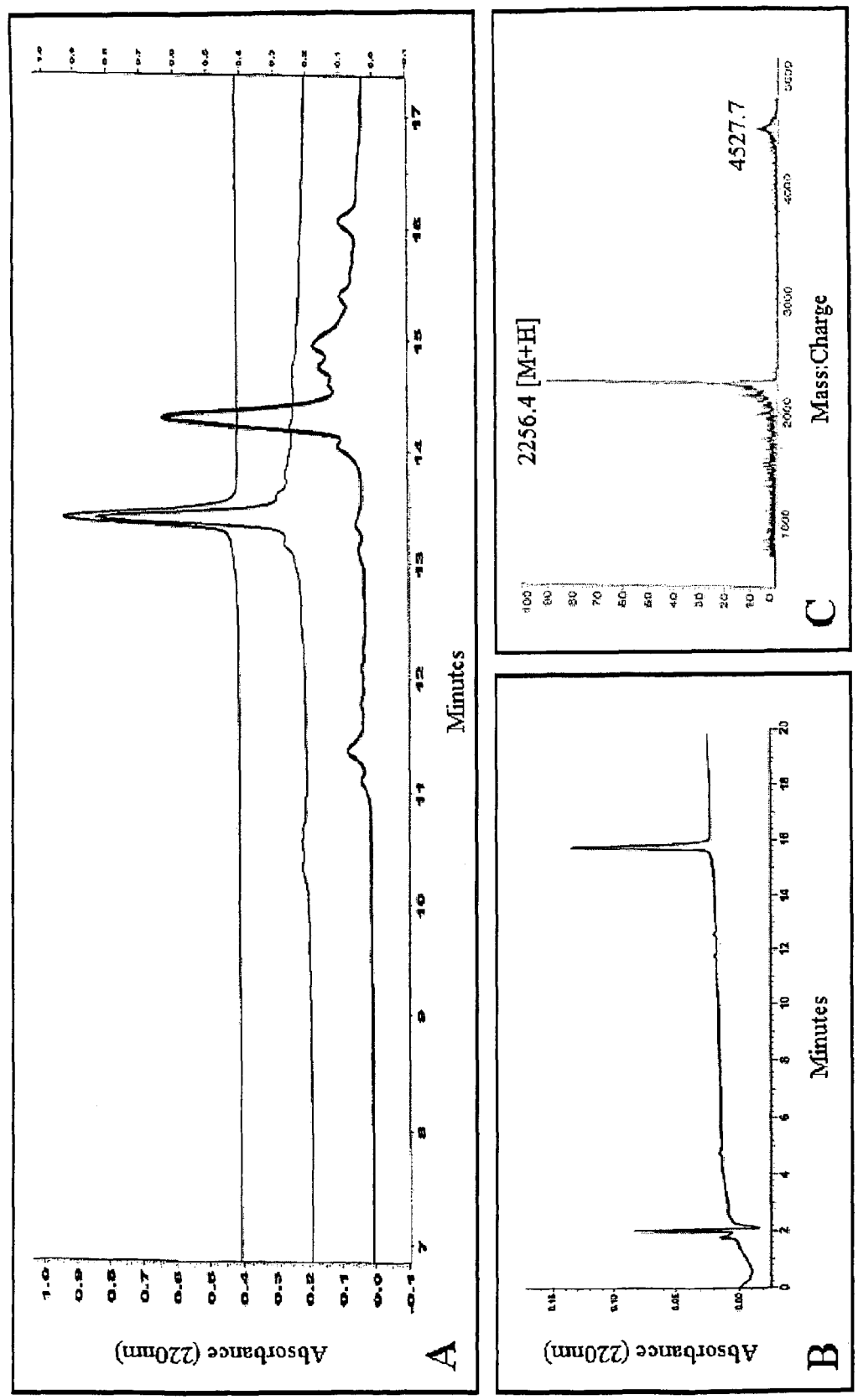
FIG. 6, Panel A illustrates a reverse phase—high performance liquid chromatography (RP-HPLC) oxidation profile.

Synthesis, Refolding, and Purification of Bioactive Bass Hepcidin. The Fmoc-amino acids derivatives were obtained from Bachem AG (4416 Bubendorf, Switzerland) and included the following side chain protected derivatives Arg (Pmc), Asn(Trt), and Cys(Trt). Stepwise assembly was carried out on a Labortec SP6000 peptide synthesizer at the 5 mmol scale starting with Fmoc-Phe-Resin. Each coupling was monitored for completeness using the ninhydrin procedure. All couplings were mediated by dicyclohexylcarbodiimide in the presence of 2 equivalents of 1-hydroxybenzotriazole. Following final removal of the Fmoc-group from the peptide resin, 1.0 g of resin-bound peptide was cleaved from the solid support and simultaneously deprotected using reagent K for 2 h at room temperature. Following cleavage, the peptide was filtered to remove the spent resin beads and precipitated with ice-cold diethyl ether. The crude peptide was collected on a fine filter funnel and washed with ice-cold diethyl ether, yielding 285 mg of crude linear peptide. The crude peptide was subsequently dissolved with 50% (v/v) AcOH in H$_2$O. The crude, solubilized peptide was subsequently diluted into 1.6 l of an aqueous buffer containing 2 M guanidinium HCl, 10% isopropyl alcohol, and 10% DMSO. The pH of the peptide solution was adjusted to 5.8 with NH$_4$OH and allowed to undergo oxidative folding at room temperature for 18 h. Following oxidation of the disulfide bonds, the peptide solution was acidified to pH 2.5 and pumped onto a Vydac C$_{18}$ column (2.5×30 cm). The sample was eluted at a flow rate of 8 ml min$^{-1}$ with a stepwise gradient from 10%, 20% and 40% acetonitrile into H$_2$O containing 0.1% TFA to concentrate the sample. Each of the fractions was analyzed by MALDI and RP-HPLC. The 40% fraction containing the refolded hepcidin was lyophilized resulting in 135 mg of approximately 40% pure peptide. This fraction was further purified using the same semi-preparative RP-HPLC column and flow rate and a gradient of 10-45% MeCN into 0.1% TFA in H$_2$O over 120 min. The resulting fractions were analyzed using two analytical RP-HPLC systems: TFA and triethyl amine phosphate (TEAP). Pure fractions were pooled and lyophilized. Upon lyophilization, 8.2 mg of bass hepcidin was obtained, representing a yield of 2.9% (FIG. 6, Panel A). Co-elution of a 1:1 mixture of the purified, native bass hepcidin with purified, synthetic hepcidin revealed a single peak (FIG. 6, Panel B).

Amino Acid and MALDI-TOF Mass Spectral Analysis. Synthetic peptide samples were hydrolyzed in 6 N HCl at 110° C. for 22 hr in vacuo. Amino acid analysis was performed on a Beckman 126AA System Gold amino acid analyzer. MALDI-TOF MS analysis was performed on a Kratos MALDI-TOF mass spectrometer using CCA as a matrix. Amino acid analysis of purified synthetic bass hepcidin showed the following average amino acid ratios: Asx (2) 2.05, Ser (1) 1.00, Pro (1) 0.97, Gly (3) 3.00, Met (1) 0.31, 0.99, Phe (2) 2.18, Val (1) 0.78, Arg (2) 1.82, and Cys (8) 5.46 (both Cys and Met are partially destroyed during the acid hydrolysis method used). MALDI-TOF mass spectral analysis of the purified synthetic bass hepcidin determined a (M+H) of 2256.4 that was consistent with the molecular mass of the native peptide (2255.97 MH$^+$) (FIG. 6, Panel C). In addition, the synthetic and native bass hepcidin gave the same dose response killing-curve against *E. coli*. These observations lead us to conclude that the two molecules are identical. Interestingly, the MALDI-TOF mass profile showed the presence of a non-covalent dimer as a sodium adduct. This species is consistent with observations in other defensin-like peptides that are known to self-associate and form aggregates. Further optimization was achieved by increasing the organic alcohol concentration to 15%, whereby the yield improved to 9%. Without isopropanol, the yield was effectively 0%, as no correctly folded material was detected when samples taken from the HPLC purification were screened for activity. The use of the co-solvent alcohols with the oxidative reaction of DMSO offer a dramatic improvement over simple DMSO mediated methods at alkaline pH or with chaotropic agents.

Polyclonal antibody production. One aspect of this invention involves development of high-titer polyclonal antibodies to the mature, folded, bioactive hepcidin. High-affinity polyclonal antibodies raised against the mature, folded, bioactive hepcidin will allow development of a sensitive and highly specific EIA assays for the measurement of the concentration and localization of bioactive hepcidin in fluids and tissues extracts.

Conjugation of linear bass hepcidin to keyhole limpet hemocyanin (KLH). To examine the potential utility of antibodies raised to the full length, mature linear hepcidin peptide SEQ ID NO:19 (GCRFCCNCCPNMSGCGVCCRF) for ELISA development, we used maleimide activated keyhole limpet hemocyanin (mcKLH-Pierce, Rockford, Ill.) for conjugation of purified, linear bass hepcidin via cysteine residues present on both KLH and the peptide. Two mg of HPLC purified linear bass hepcidin was dissolved in 300 µl of 4 M guanadine HCl, pH 6.8 and immediately mixed with two mg KLH in a total volume of 500 µl. The reaction mixture was left at RT for two hours. No precipitation of the protein-peptide conjugates was observed over the first hour, but precipitation was clearly apparent after two hours. The conjugation mixture was centrifuged to pellet the precipitate protein-peptide conjugate and the supernatant removed. The soluble conjugate was subsequently desalted by gel filtration and the protein concentration of the recovered fractions determined. Recovery of soluble conjugate totaled ~600 µg. The soluble conjugate was then combined with the precipitated conjugate (~3 mg), resuspended by vigorous pipetting, and stored at −20° C. until further use.

Conjugation of refolded bass hepcidin to KLH. Two additional conjugates were developed for polyclonal antibody production by taking advantage of the only available (N-terminal) primary amine group present in refolded bass hepcidin for conjugation to KLH using EDC (1-Ethyl-3-[3-Dimethylamino-propyl] carbodiimide HCl) and DSS (Disuccinimidyl suberate) chemistries. EDC promotes peptide conjugation to carrier proteins via primary amines and carboxyl groups, while the homobifunctional crosslinker, DSS, is primary amine reactive and links peptides to carrier proteins primarily through lysine residues.

EDC mediated conjugation of bass hepcidin to KLH. EDC mediated conjugation of bass hepcidin to KLH was performed using the Imject® Immunogen EDC Conjugation Kit essentially as recommended by the manufacturer (Pierce, Rockford, Ill.). Two mg of partially purified refolded bass hepcidin was dissolved in 600 µl conjugation buffer containing DMSO (16.67%), which formed a slightly yellow solution containing some insoluble material. Undissolved material was removed by centrifugation and 500 µl of cleared supernatant was removed and added to 2 mg of KLH in 200 µl of dH$_2$O. EDC reagent was dissolved in water and immediately added to the protein-peptide solution and the mixture vortexed moderately. The reaction mixture was allowed to stand at RT for two hours. A fine micro-precipitate was seen to form after ~10 minutes and was present at two hours, however, very little precipitate was recovered following centrifugation at 21,000×g. The conjugation mixture was desalted by gel filtration and the protein concentration determined. A total of 3 mg of conjugate was present in the soluble fraction and we estimated the insoluble to be <1 mg. Soluble and insoluble conjugate were combined, resuspended, and stored at −20° C.

DSS mediated conjugation of bass hepcidin to KLH. Two mg of partially purified bass hepcidin was dissolved in 50 µl of DMSO and 2 mg KLH was dissolved in 900 PI phosphate buffered saline (PBS, pH 7.4) and vortexed. 40 µg of DSS dissolved in DMSO was added to the KLH solution and left at RT for 8 minutes to allow DSS to react with KLH. At 8 minutes, 50 µl of the bass hepcidin solution was added to the DSS-KLH reaction mixture and vortexed. The reaction mixture was incubated at RT for 30 minutes when 50 µl of 1 M TRIS-HCl, pH 8.8 was added to block unreacted DSS molecules. A fine micro-precipitate was present following the 30-minute incubation period and was removed by centrifugation. A large pellet of precipitate was observed. The soluble conjugation mixture was desalted by gel filtration and the protein concentration determined. A total of 2.1 mg of conjugate was present in the soluble fraction and we estimated the insoluble to be <2 mg. Soluble and insoluble conjugate were combined, resuspended, and stored at −20° C.

Bass hepcidin antibody production. All antibody production was performed under AAALAC approved protocols. Two specific, pathogen free New Zealand white rabbits were immunized with each of the hepcidin-KLH conjugates following collection of 5 ml of pre-immune serum. Each of the conjugates contained precipitated material and required resuspension before the primary immunization and each subsequent booster immunization. Conjugates were resuspended by repeated passage through a 24-gauge needle. Primary immunization was conducted with ~200 fig of the conjugate that was homogenized in a highly refined Freund's Complete Adjuvant. Booster immunizations were performed with 100 µg of the conjugate in highly refined Freund's Incomplete Adjuvant. Both the primary and the booster immunizations were administered in a single subcutaneous site. Serum collected from bleeds was collected and monitored for antibody response to the mature, folded, bioactive hepcidin.

Determination of anti-bass hepcidin titers. Anti-bass hepcidin antibody titers were determined by coating maleic anhydride activated 96 well microtiter plates with a constant amount (125 ng) of refolded bass hepcidin. After incubation overnight at 28° C., the plates were blocked using Pierce SUPERBLOCK™ in tribuffered saline (TBS, 3× for 5 minutes at 28° C.). Dilutions of the pre-immune, test bleed, and production bleed sera (1:500 or 1:4000) were placed in duplicate wells, serial 2-fold dilutions were performed to 1:32,000 or 1:256,000, respectively, and the plates incubated for 2 h at 28° C. After 3 washes with PBS containing 0.05% TWEEN-20 ™ (PBS-T20), rabbit anti-bass hepcidin-specific immunoglobulin was detected using a 1:10,000 dilution of horseradish peroxidase (HRP)-conjugated-goat anti-rabbit IgG antibody (Pierce, Rockford, Ill.). Following a 30 min incubation at 28° C., the plates were washed again (PBS-T20), 1-STEP TURBO TMB™ substrate was added to all wells, and the reaction was allowed to develop for 15 min. Development was halted by the addition of a stop reagent and the optical density (OD) was measured at 450 nm with a Molecular Devices VMAX KINETIC™ microtiter plate reader.

Anti-linear bass hepcidin titers. The rabbit anti-linear hepcidin-KLH-conjugate serum failed to recognize the mature, refolded, bioactive, hepcidin peptide. Thus, adequate titers of this antibody were not detected. The pre-immune sera from these rabbits appeared to cross-react with the refolded bass hepcidin resulting in high non-specific background roughly equivalent to the entire response seen in the test and production bleeds.

Anti-mature, folded, bioactive bass hepcidin antibody titers. Screening of the test bleed sera at five weeks post-immunization demonstrated that both rabbits developed acceptable titers to the EDC hepcidin-KLH conjugate. However, only one of the two rabbits developed an acceptable titer when immunized with the DSS hepcidin-KLH conjugate. The titer was expressed as the dilution at which the OD of the immunized serum exceeded that of the pre-immune serum (i.e. background) by at least 0.1 units. The titer was calculated by setting x=0.1 in the linear regression equation that was derived from plots of the inverse of the dilution versus the corrected OD, i.e. the observed OD minus OD of pre-immune serum. Anti-refolded bass hepcidin titers were estimated to be 12,500 and 26,500 at 5 weeks post immunization with the two KLH-conjugates prepared using EDC chemistry (KST 3, KST 4), respectively. The titer the conjugate prepared using DSS chemistry was estimated to be 8,000. Anti-mature, folded, bioactive hepcidin antibody titers increased significantly by 7 weeks post-immunization in production bleed #1 in all four sera tested and were estimated to be 70,000 for KST 3, 163,000 for KST 4, and 35,000 for KST 5.

Protein A Affinity purification of bass hepcidin antibodies. To further examine the specificity of these antibodies for hepcidin, we performed Protein A affinity purification according to manufacturer's instructions (Pierce). Aliquots of each of the two sera (KST 3, KST 4) were diluted in IMMU-NOPURE™ binding buffer 1:2 and applied Protein A affinity column (3 ml) mounted on a low pressure chromatography system and washed extensively with binding buffer. Antibodies were eluted using IMMUNOPURE™ Elution Buffer, neutralized by addition of 1 M Tris-HCl, pH 7.5, and dialyzed against PBS. Protein concentrations were determined using the BCA protein assay.

Affinity purification of anti-mature, folded, bioactive hepcidin antibodies. Approximately 2 mgs of the mature, folded hepcidin peptide was coupled to 2 ml (wet volume) of cyanogen activated Sepharose 4B using essentially the manufacturers instructions. Polyclonal anti-hepcidin rabbit sera was diluted in PBS and passed over the column at a flow rate of 1 ml/min, and subsequently washed thoroughly with 10 column volumes of PBS. Bound antibodies were eluted with glycine buffer, pH 2.5 and immediately neutralized by addition of 1 M Tris, pH 8. Antibodies were then dialyzed against PBS, concentrated, and stored at 4° C. until further use. ELISA comparisons between affinity purified antibodies and Protein A affinity purified antibodies clearly demonstrated enhanced signal and reduced background. Competition experiments with synthetic hepcidin demonstrate that >90% of the signal from the hepcidin affinity-purified antibodies can be competed away. This is in contrast to Protein A affinity purified antibodies and serum, where ~80% and ~65%, respectively, of the signal was competed. Higher signal to noise ratios were also observed in Western blots and immunohistochemical analysis of hepcidin expression in HSB tissues described below.

Figure 10:
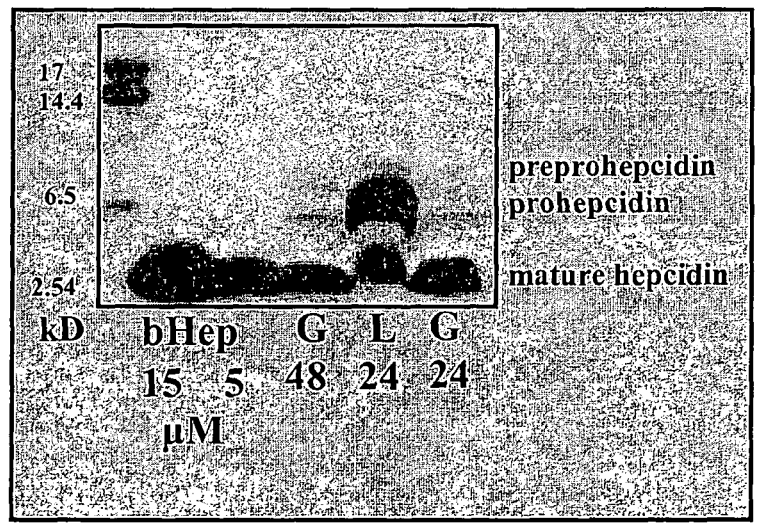
FIG. 10 depicts a Western blot of synthetic bass hepcidin and of a partially purified, native bass hepcidin, 24 and 48 h after infection with *Streptococcus iniae*.

Western Blot analysis of purified HSB extracts using affinity purified anti-hepcidin antibodies. Adult hybrid striped bass were challenged with an intraperitoneal injection of live S. iniae (K288, 100 μl of a logarithmic phase culture at $2.10^7$ cfu/ml). Gill and liver tissue were harvested at 24 and 48 h after bacterial challenge and immediately frozen by immersion in liquid nitrogen. Frozen samples were ground into powder with a mortar and pestle under liquid nitrogen. Proteins were extracted in 10% acetic acid by shaking on ice-cold water bath for 2-3 h. After centrifugation, (2800×g for 20 min), the supernatants were filtered (0.45 μm, MILLEX™; Millipore Corp.), and loaded onto SEP-PAK™ C18 cartridge (Waters Associates) equilibrated with 10% acetic acid to concentrate extracted cationic peptides. The cartridges were washed with acidified water (0.05% trifluoroacetic acid), and elution was performed with 30% acetonitrile, 0.05% trifluoroacetic acid. Eluted material was lyophilized, the protein powder weighed, and re-suspended at 10 mg/ml (w/v). 6.5 μl of the 10 mg/ml extracts were prepared as instructed with NuPAGE loading solution, loaded on NUPAGE™ Novex Bis-Tris Gel and run at 200 V for 30 min. Proteins were transferred onto a PVDF membrane (45 min at 30V). The membrane was blocked with BSA 3.3% in TBS, 0.1% TWEEN-20™ for 1 h. Affinity purified rabbit anti-mature, folded, bioactive hepcidin antibody (KST4) (0.7 mg/ml) was used at 1/10,000 dilution in Tris Buffer Saline (TBS), 0.2% TWEEN-20™, BSA 2%. After an overnight incubation at 4° C. the membrane was washed with TBS TWEEN-20™ 0.2% twice rapidly, and for 30 min by changing the washing solution every 5 min. The secondary antibody (HRP-conjugated AFFINIPURE™ Goat Anti-Rabbit IgG, Jackson Immuno Research) was used at 1/10 000 dilution in 1% BSA TBS, 0.2% TWEEN-20™. After 1 h incubation at room temperature the membrane was washed using the same conditions as described earlier and the blot was revealed by photoluminescence and film following manufacturers instructions (ECL kit, Amersham; FIG. 10). The results of this Western Blot analysis of the native forms of bass hepcidin using the anti-bass hepcidin affinity purified KST 4 antibodies demonstrate several critical aspects of the claimed methods and inventions involving refolding hepcdin polypeptides and antibody development to the mature, folded, bioactive hepcidin described in this application. These antibodies clearly recognize a native form of the HSB hepcidin in Western Blots, that is of the same molecular weight as the synthetic, mature, folded, bioactive hepcidin (2.54 kD). These affinity-purified antibodies were capable of detecting the pro-hepcidin, and pre-prohepidin forms in these experiments, presumably due the same reasoning (see FIG. 10, lanes 4-6). It is also known in the art, that antibodies raised to fragments of the mature human hepcidin linear polypeptide, fail to yield signal when tested against the mature, folded, bioactive form found in serum, by ELISA. This is exactly the observation we made following analysis of our titer experiments described above. Hepcidin is strongly expressed in liver of HSB following infection with the Gram-positive S. iniae, with prohepcidin being the predominant form detected, although significant amounts of the mature hepcidin peptide are present as well. In contrast, the mature form is observed in high concentration in gill. Pre-prohepcidin and prohepcidin are observed in HSB gill tissue following infection, confirming our previous hepcidin purification results and kinetic RT-PCR, gene expression studies in gill following infections with S. iniae. (see FIG. 10, lanes 4 and 6). These results support the utility and several other embodiments of the inventions described herein.

Development of bass hepcidin enzyme/ligand conjugates for ELISA. We took advantage of the only available (N-terminal) primary amine group present in refolded bass hepcidin for conjugation to KLH using EDC (1-Ethyl-3-[3-Dimethylamino-propyl] carbodiimide HCl) and DSS (Disuccinimidyl suberate) chemistries. These approaches were very difficult to develop and apply to production of hepcidin conjugates due to hepcidin's inherent solubility issues in higher pH coupling buffers. Our studies have demonstrated that bioactive hepcidin is very sensitive to salt in solution and readily aggregates at relatively low concentrations (50 ng ml$^{-1}$) in phosphate buffered saline (PBS; pH 7.4) but can be dissolved with vigorous vortexing at RT. We have encountered significant issues when trying to solubilize hepcidin at the higher concentrations (1-3 mg ml$^{-1}$) in standard coupling buffers desirable for production of high activity, soluble hepcidin-HRP conjugates for ELISA.

Synthesis and purification of derivitized hepcidin to produce validated hepcidin-biotin conjugates for enzyme linked immunosorbent assays (ELISA). We successfully synthesized and refolded bass hepcidin containing two [2-(2-Amino-Ethoxy) Ethoxy] Acetic Acid (AEEAc) residues at the amino terminus in an effort to (i) enhance the solubility of the peptide, and (ii) add two spacer amino acid analogs to reduce any steric or electrostatic hinderance that may occur between enzymes/ligands and the cationic hepcidin peptide. AEEAc is a hydrophilic spacer molecule that can be readily coupled to other proteins. Oxygen species in AEEAc residues greatly enhanced the solubility of hepcidin and allowed us to readily couple biotin to hepcidin to produce a conjugate for ELISA. We used EDC chemistry for production of this conjugate as we have described previously. This conjugate proved to have very low non-specific binding in our ELISA, allowing development of a sensitive, competitive ELISA for hepcidin.

Competition ELISA Protocol. A high-binding 96-well microplate (Corning, Inc., Cat. No. 3590) was coated with 100 µl of a 1:5,000 dilution of affinity-purified rabbit anti-HSB hepcidin antibody (0.68 mg/ml) in carbonate-bicarbonate coating buffer pH 9.6 (Sigma-Aldrich Corp., Cat. No. C-3041). One well contained 100 µl carbonate-bicarbonate coating buffer and no antibody. The plate was covered and placed at 4.degree.C. Following a suitable period of incubation at 4.degree. C., the plate was washed with three, 300 µl volumes of PBS-T (PBS containing 0.05% TWEEN-20™). Next, the plate was blocked with 250 µl of a 2% (w/v) dry milk solution in PBS, covered, and incubated for one hour at RT, shaking at 150 rpm. Samples and standard curves were prepared in a separate 96-well plate. Serum, plasma, and urine samples were diluted with PBS diluted to be within the working range of the standard curve. An aliquot of biotinylated AEEAc-derivatized hepcidin (0.21 mg/ml diluted 1:2000) was added to each well to give a final biotinylated hepcidin concentration of 94.5 ng/ml. From each well of the sample/standard curve dilution plate, 100 µl was transferred to the antibody coated and blocked plate. The plate was covered and incubated at RT, shaking at 150 rpm, for 1 hour to allow competitive binding to occur. After incubation, the plate was washed three times with 300 µl PBS-T. Next, 100 µl of a 1:5000 dilution of strepavidin-HRP (Jackson ImmunoResearch Laboratories, Inc.) in PBS was added to each well. The plate was covered and incubated at RT, shaking at 150 rpm, for 30 minutes. Following incubation the plate was washed four times with 300 µl PBS-T. A 100 µl volume of tetramethylbenzidine (TMB) substrate (Moss, Inc.) was added to each well. The plate was allowed to develop for 15 minutes then was stopped with 100 µl of 0.5 N $H_2SO_4$. Absorbance at 450 nm was determined using a THERMOMAX™ microplate reader with SOFTMAX PRO™ software (Molecular Devices). Data were analyzed using a spreadsheet program. A standard curve was fit using a logarithmic, exponential, or power regression. Sample dilutions producing OD values lying within the most informative range of the curve were used to compute hepcidin concentrations. Two standard curves were run in the first two columns of the dilution plate by serially diluting 100 and 10 µg/ml stock native hepcidin solutions down the plate. Two wells received PBS with no hepcidin competitor. Next, biotinylated AEEAc-derivatized hepcidin (0.21 mg/ml diluted 1:2,000 in PBS) was added to each standard curve well including a background well and a no competition well to yield a biotinylated hepcidin concentration of 94.5 ng/ml in each well. Standard curve had final hepcidin concentrations of 10,000, 5,000, 2,500, 1,250, 625, 312.5, 156.3 and 1,000, 500, 250, 125, 62.5, 31.3, 15.6 ng/ml (see FIG. 9 for a representative standard curve).

Immunohistochemical Tissue Collection and Processing. Tissues were quickly removed from moribund animals and were placed in roughly 10-20 equivalent volumes of Bouin's fixative overnight (approx 15-18 hours) at room temperature. The following day tissues were rough trimmed into cassettes, held in 70% ethanol and submitted for routine histological processing. Tissues were embedded in paraffin, and 5 µM sections were cut and adhered to glass microscope slides were prepared by routine procedures. The slides were held at room temperature in a slide box until required for immunohistochemical staining. Prior to IHC, all sections are deparaffinized in 3 xylene washes, followed by two absolute ethanol and one 95% ethanol wash, and held submerged in deionized water until ready for probing with the primary antibody. Sections were then transferred to 0.01 M phosphate buffered saline (PBS, containing 0.138 M NaCl, 0.0027 M KCl) for 10 min and held until IHC staining was performed.

IHC Methodology. Detection of the primary anti-mature, folded, bioactive hepcidin antibody probe overlayed on tissue sections was performed using a commercially available rabbit antibody detection kit (HISTOSTAIN PLUS™, Zymed Laboratories Inc., San Francisco, Calif.). Prior to applying the primary antibody (previously affinity purified against mature refolded, bioactive bass hepcidin) the endogenous tissue peroxidase activity was quenched by submerging slides in a solution containing 1 part hydrogen peroxide (30% activity) and 9 parts absolute methanol for 30 min. Following this the slides were washed 3 times in PBS, the sections were blocked for 30 min and each slide was probed with rabbit anti-bass hepcidin antibody (1:1000 dilution in PBS) and incubated at room temperature (22-24° C.) overnight in a humid chamber. The following day the slides were washed 3 times in PBS then flooded with biotinylated goat anti-rabbit antibody, incubated for 30 min and washed as described. The HRP:streptavidin enzyme conjugate was applied for 15 min, removed with three PBS washes, the chromogen (AEC) incubated for an additional 10 min and all slides were then rinsed twice with distilled water. Tissues were counterstained with hematoxylin for 10 min, washed twice with distilled water (2 min each) and briefly immersed in PBS for 1 min. Several drops of GVA mounting medium were applied to each section and a coverslip was placed over the stained tissues. The mounting medium was allowed to dry overnight on the bench top at room temperature. Tissues that contained hepcidin contained a characteristic red-brown precipitate throughout, compared to control tissues that gave a very weak but similarly colored background signal.

Microbial Isolates. *Aeromonas hydrophila, A. salmonicida, Edwardsiella tarda, Plesiomonas shigelloides,* and *S. iniae* were laboratory isolates recovered from moribund hybrid striped bass (HSB, Kent SeaTech Corp.). Biochemical analysis and ribosomal DNA (16S) sequencing were used to confirm their identification. Logarithmic phase cultures were used in all experiments. Most bacteria and yeast were grown in Luria-Bertani Broth (LB, Difco), although streptococcal isolates were grown in Todd Hewitt Broth (THB, Difco). Filamentous fungi were grown in half-strength potato dextrose broth (Proteine Data Bank, hereinafter PDB, Difco) supplemented with tetracycline (10 µg/ml).

Antimicrobial Assays. Minimal inhibitory concentration (MIC) for liquid growth inhibition assay and minimal bactericidal concentration (MBC) were determined as described previously. Briefly, bacteria, yeast, and filamentous fungi were incubated in the appropriate growth media in the presence of 2-fold serial dilutions of synthetic bass hepcidin (44-5.5 µM final concentrations). Bacterial growth was measured ($OD_{600}$) after 18 h incubation at 37° C. MIC was expressed as the lowest concentration of peptide tested that inhibited microbial growth completely. For determination of MBC, bacteria were incubated in 96-well plates in the presence of varying concentrations of hepcidin for 18 h at 37° C., then aliquots of the cultures were plated on Todd Hewitt agar and bacterial growth was assessed after overnight incubation at 37° C. To examine the rate of bacterial killing of bass hepcidin, kinetic studies were performed using the Gram-negative pathogen, *Yersinia enterocolitica*. Briefly, synthetic bass hepcidin (22 and 44 μM), or moronecidin (10 μM) was added to a log phase culture of *Y. enterocolitica* ($2\times10^5$ CFU ml$^{-1}$) and incubated at 37° C. Bacterial viability was assessed at times 0, 0.5, 1, 2 and 3 h by plating serial dilutions of the bacterial suspension on Todd Hewitt agar. CFU counts were performed after overnight incubation at 37° C. The growth index was calculated as bacterial CFU recovered/CFU at time zero.

Antimicrobial Synergism Studies. Synergism between synthetic bass hepcidin and moronecidin was tested in checkerboard liquid growth inhibition assays. In brief, two-fold serial dilutions of each peptide were made in water, and 10 μl of the solution added to the bottom of the wells of a 96-well plate. Ninety μl of exponential phase bacterial cultures ($OD_{600}$~0.2) were freshly diluted in culture media to ~$2\times10^5$ CFU ml$^{-1}$ and added to peptide solutions. Controls consisted of wells with the appropriate volume and concentration of each peptide alone, or of water. Bacterial viability was assayed at 2 h by plating aliquots of the bacterial suspension for CFU enumeration. The bacterial suspensions were further incubated overnight at 37° C. and bacterial growth was monitored by optical density at 600 nm for determination of MIC. Synergistic activity was quantify as fractional inhibition concentration (FIC) index=$([A]/MIC_A)+([B]/MIC_B)$, where $MIC_A$ and $MIC_B$ are the MICs of the peptides alone and [A] and [B] are the MICs of A and B when used together.

Germination and Fungicidal Assay. Spores of *A. niger* were harvested and resuspended in sterile water containing 0.05% TWEEN-80™, and the concentration adjusted to approximately $10^8$ spores per ml. Spores were diluted in half-strength PDB containing 16 μM chloramphenicol to a final concentration of $10^5$ spores per ml. Ninety μl of the suspension was placed in sterile flat-bottomed polystyrene 96-well plates with 10 μl of serial dilutions of peptide (440 μM, 220 μM, 110 μM, 55 μM), in water. Germination of spores was allowed to proceed for 2 days at 30° C. in the dark, after which hyphae density was measured by absorbance at 600 nm. After 2 days of incubation, the contents of wells showing no germination were centrifuged for 3 min at 5000 rpm, resuspended in 50 μl of fresh PDB media, and triplicate aliquots spotted onto PDB agar plates. Plates were placed at 30° C. for 3 days to monitor germination of hyphae. The absence of germination indicated fungicidal activity.

Hemolytic activity. Freshly packed striped bass erythrocytes (3 ml) isolated from young fingerlings (~30 g) and adult fish (~300 g) were washed with phosphate-buffered saline (PBS; pH 7.4) until the supernatant was colorless and resuspended in PBS (30 ml) supplemented with glucose (0.2%, w/v). Synthetic bass hepcidin (10 μl of 880-55 μM) was added to 90 μl of a 1% suspension of washed erythrocytes in microcentrifuge tubes. Triplicate samples were incubated for 30, 90, 180, and 240 min at 37° C. then centrifuged for 10 min at 3500 rpm. Supernatant from the erythrocyte suspension (70 μl) was placed in a microtiter plate and optical density at 405 nm determined. The percentage of hemolysis in hepcidin-treated erythrocytes was expressed relative to hemolysis obtained with a control erythrocyte suspension treated with 0.1% sodium dodecyl sulphate (SDS, 100% hemolysis).

Development of a competitive reverse transcriptase/polymerase chain reaction (cRT-PCR) tool for measurement of hepcidin gene expression in vertebrate animals. To characterize bass hepcidin expression levels in response to infections against the Gram-positive (*S. iniae*) and Gram-negative pathogens (*A. salmonicida* and a *Piscirickettsia*-like Organism; PLO) affecting vertebrate animals, we developed and optimized a cRT-PCR. Briefly, this assay is based on competition during an RT-PCR reaction between the native mRNA target (i.e. bass hepcidin mRNA) and a synthetic competitor mRNA (cRNA) that is constructed to serve as an internal standard used to quantify native mRNA levels. The synthetic cRNA is designed to have nucleotide sequence and primer binding sites which are identical to the target native mRNA, but also contains a deletion (or insertion) to allow discrimination between the native mRNA and the cRNA following gel electrophoresis. To perform this assay, a series of RT-PCR reactions are run using decreasing amounts of the competitor RNA in the presence of a known constant amount of total RNA (or mRNA) from an experimental tissue sample. Signal strength of resulting PCR products from both the target RNA and competitor RNA are compared using digital densitometry analyses of the PCR amplicons and regression analysis. Since the amount of cRNA in each reaction is known, the amount of target native mRNA can be estimated at the point of signal equivalence (i.e. Target:Competitor ratio=1:1).

Method for development of an expression vector for production of a bass hepcidin mRNA competitor. RT-PCR analysis of gene expression is based on reverse transcription of the target mRNA templates to produce cDNA copies which then serve as templates for amplification of the target region by standard PCR methods.

FIG. 1 is a sequence listing illustrating the copy DNA (cDNA) and predicted amino acid sequence of white bass hepcidin. Primer binding sites are shown with arrows (5' to 3'). The organization of the peptide domains (signal peptide, prodomain, and mature peptide) is shown by amino acid sequence enclosed by a . The stop codon is indicated with an asterisk. Location of introns, and the predicted peptide cleavage site are also shown, in accordance with the present invention.

Figure 2:
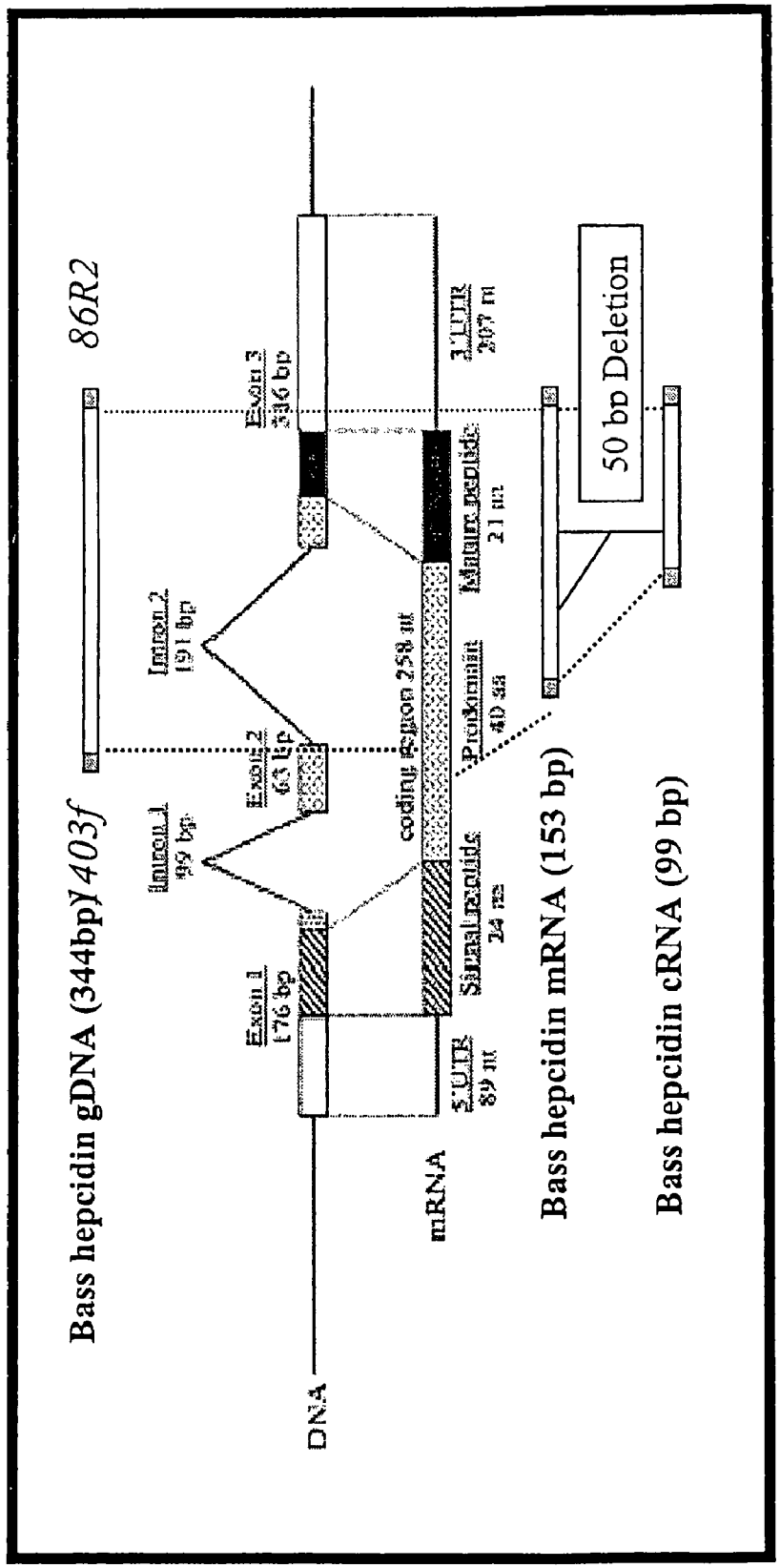
FIG. 2 is a diagrammatic illustration of gene organization, genomic DNA, and mRNA regions coding related to a signal peptide, a prodomain, and the mature peptide of white bass, in accordance with another aspect of the present invention.

Since PCR artifacts resulting from target genomic DNA (gDNA) contamination in the purified RNA can impair the accuracy of an RT-PCR assay, we designed PCR primers on each side of a intron splice site in the gene of interest. Primers designed in this manner would amplify two amplicons in a simple RT-PCR assay (three in cRT-PCR) where contaminating gDNA was present, with the larger amplicon derived from the gDNA template. The size of the larger amplicon would correspond to the expected amplicon size plus the number of base pairs present in the intron. To construct an expression vector for production of a bass hepcidin cRNA, we synthesized two single stranded DNA oligonucleotides of 64 and 74 nucleotides. One oligonucleotide had a sequence identical to a portion of the plus strand in exon 2 and exon 3 and spanned the intron 2 splice site of bass hepcidin. The second oligonucleotide had a sequence identical to a portion of the minus strand in exon 2 and 3 and spanned the Intron 2 splice site as well. The oligos were also designed to include a 50 base pair (bp) deletion of coding sequence and 30 bp of overlapping complementary sequence near each of their 3' ends. Following synthesis, equimolar concentrations of the two oligonucleotides were hybridized to each other in a standard annealing reaction and made double-stranded by primer extension using standard techniques. The resulting 108 bp double-stranded product contained RT-PCR primer binding sites used to amplify the target region (intron 2 splice site) of the bass hepcidin mRNA. The internal 50 bp deletion in the cRNA expression vector construct was engineered to allow simple electrophoretic differentiation between amplicons derived from native mRNA and cRNA. In FIG. 2, there is shown a diagrammatic illustration of gene organization, the size and arrangement of the introns and exons of the white bass hepcidin genomic DNA, as well as the corresponding mRNA regions coding for a signal peptide, a prodomain, and the mature peptide regions.

Method for development of cRT-PCR tools for vertebrate animals. Hepcidin gene expression in infected and mock-challenged HSB fingerlings was quantified using a competitive RT-PCR assay. A homologous RNA competitor (designated as 'cHEP') was constructed using a segment of the bass hepcidin prodomain containing a 50 bp deletion spanning two RT-PCR primer binding sites: 1403F2 (SEQ ID NO:1)(5'-GAGATGCCAGTGGAATCGTGGAAG-3') and 86R2 (SEQ ID NO:2)(5'-GAGGCTGGAGCAGGAATCCTCAG-3'). The amplicon resulting from RT-PCR of the competitor hepcidin mRNA ('cHEP': 99 bp) was designed to be easily discernable from the native bass hepcidin mRNA ('bHEP': 153 bp) using agarose gel electrophoresis. To generate the competitor, equimolar concentrations of two oligonucleotide primers cHEP1 (SEQ ID NO:3) 5' GGATCCGAGATGC-CAGTGGAATCGTGGAAGTTGCTGCAT-TGCTGTCCTAATATGAGCGGATGTGGT-GTCTGCTGC3') and cHEP2 (SEQ ID NO:4) 5' GGATCCGAGGCTGGAGCAGGAATCCTCA-GAACCTGCAGCAGACACCACATCCGCTCA TATT-AGG3') were annealed using standard conditions, yielding a 109 bp product with 30 bp of complementary overlap, and the product was amplified with the primer pair 1403F2 and 86R2. Purified PCR product was cloned into pCC 1, which contained an upstream T7 RNA polymerase promoter, following the manufacturer's instructions (COPYCONTROL™ pCC 1 PCR Cloning Kit; Epicentre). Approximately 100 ng of plasmid vector, containing the modified hepcidin prodomain segment, was linearized with Hind III (Invitrogen) downstream of the insertion site and in vitro transcription was performed using a T7 RNA polymerase ( DURASCRIBE T7 TRANSCRIPTION KIT™; Epicentre). Competitor RNA was purified, treated with DNAase, and resuspended in RNAase-free water following manufacturer's instructions (RNEASY PURIFICATION KIT™; Qiagen). Ribonucleic acid (RNA) concentrations were measured and aliquots of 10-fold serial dilutions were made (10-0.0001 ng/µl) and stored at −80° C.

Clinical studies using cRT-PCR, tissue collection, and RNA extraction. Thirty HSB fingerlings (43.35 g+17.51 g) were injected intraperitoneally (IP) with S. iniae ($3.5 \times 10^5$ CFU) or A. salmonicida ($2.0 \times 10^5$ CFU). Fish injected with sterile PBS served as controls. Following challenge, the three groups of fish were maintained in separate 60 L flow-through tanks receiving aerated water at 25° C.+0.1° C. For mRNA expression analysis, two individual fingerlings from each challenged group (S. iniae and A. salmonicida) were selected randomly at five time points post-challenge (4, 8, 16, 24, and 48 h) and anesthetized with MS-222 (Finquel; Argent). Liver tissue (~300 mg) was dissected aseptically and preserved in RNALATER™ (Ambion). Liver samples were also collected from the control group (i.e. PBS) pre-challenge (0 hr), and at two time points (8 and 24 h) post-challenge. The remaining fingerlings in each group were monitored daily for morbidity and mortality; tissues (brain, head kidney) from moribund animals were cultured on TSA plates containing 5% sheep blood to confirm the presence of S. iniae or A. salmonicida. Preserved liver tissues (50 mg) were homogenized in TRI-REAGENT™ (Molecular Research Center) and total RNA was extracted according to the manufacturer's protocol. An additional DNase treatment was performed to further remove any genomic DNA contamination. RNA concentrations were determined spectrophotometrically ($A_{260}$), and 50 ng $\mu l^{-1}$ working aliquots were diluted in RNAase-free $H_2O$ and stored at −80° C.

Method for quantification of hepcidin gene expression using competitive RT-PCR. To assess levels of native bass hepcidin mRNA using competitive RT-PCR (cRT-PCR), total RNA from each liver sample (infected or mock-challenged HSB) was assayed in a series of six single-tube RT-PCR reactions run in parallel. Each single-tube RT-PCR reaction contained: (a) 100 ng of total RNA extracted from the liver, and (b) one of six increasing amounts of hepcidin competitor (0.0001 ng to 10 ng). A second, non-competitive RT-PCR reaction was performed to confirm the quality of the RNA samples using PCR primers that amplify a region of 18S rRNA of HSB (SB18S, 5'-GTTCGATTCCGGAGAGG-GAG-3'(SEQ ID NO:5), SB18Srev, 5'-CCTTCCTTGGAT-GTGGTAGCC-3') (SEQ ID NO:6). In all cases, RNA was reverse transcribed and amplified in a single reaction with the primers 1403F2/86R2 or SB18S/SB18rev using the cycling profile: (1) reverse transcription for 20 min at 60° C.; (2) denaturation for 30 s at 94° C.; (3) annealing for 30 s at 58° C.; (4) extension for 30 s at 72° C.; (5) Steps 2-4 were repeated for a total of 20 cycles (6) final extension for 2 min at 72° C. Amplified products were electrophoresed on 2.0% agarose gel stained with ethidium bromide (0.05 µg $ml^{-1}$). For competitive RT-PCR assays, gel images were digitized using an EDAS 120 electrophoresis documentation system and mean fluorescent intensities of the PCR products (cHEP and bHEP) were scanned by densitometry using NIH IMAGE 1.63™. Regression curves were generated from each series of six single-tube RT-PCR reactions by plotting, on double logarithmic scale, the value of the known competitor quantity (0.0001 to 10 ng) against the fluorescent signal ratio of the resulting RT-PCR amplicons (cHEP:bHEP). The quantity of native hepcidin mRNA for each sample was determined based on the point of signal equivalence (competitor: target=1).

Semi-quantitative or qualitative cRT-PCR. One aspect of this invention, in addition to cRT-PCR and ELISA, is a simple, rapid, single tube assay for the routine monitoring of hepcidin levels in vertebrate animals, especially fish, and other mass-produced vertebrate animals where it would be difficult to collect bodily fluids for ELISA analysis. Our invention clearly demonstrates the response of both hepcidin gene expression and the production of the mature, folded, bioactive hepcidin in our clinical trials using our fish infection model. The effect of infections on hepcidin gene expression is rapid and significant, within 4-6 hours of the onset of an infection. Thus, a simple, semi-quantitative or qualitative tool for monitoring infection among populations, would be another application of this technology. A simple kit containing oligonucleotides designed as herein described, along with a set of standards, would allow practitioners to assess normal levels of hepcidin expression and detect anomalous ones within hours of obtaining a sample. We define this tool semi-quantitative competitive RT-PCR (sqcRT-PCR).

Method for sqcRT-PCR. For hepcidin sqcRT-PCR, total RNA was isolated from ~0.05 grams of liver. Following RNA quantification, a one-step/single-tube, competitive RT-PCRs (One-step RT-PCR) were performed in 25 µl reaction volumes containing 0.5 µM of each primer (1403F & 86R2), 50 ng of total RNA, and 0.1 ng of 'cHEP' (competitor hepcidin mRNA containing a 50 bp deletion) using the following cycling profile: 20 minutes at 50° C., followed by 20 cycles of 94° C. (5 seconds), 57° C. (10 seconds) and 72° C. (10 seconds), and final extension at 72° C. for 1 minute. RT-PCR products were visualized on a 1% agarose gel, stained with ethidium bromide, and photographed. Comparison of relative gene expression levels between treatment and control groups can be performed in two ways, qualitatively and semi-quantitatively. The qualitative approach involved estimating the relative level of endogenous hepcidin mRNA levels as compared to the cRNA competitor by intensity of staining of the bands and assessing the amount of competitor added (see FIG. 19, bottom panel). Semi-quantitative analysis requires an image analysis approach as described immediately above for cRT-PCR (see FIG. 16).

Figure 19:
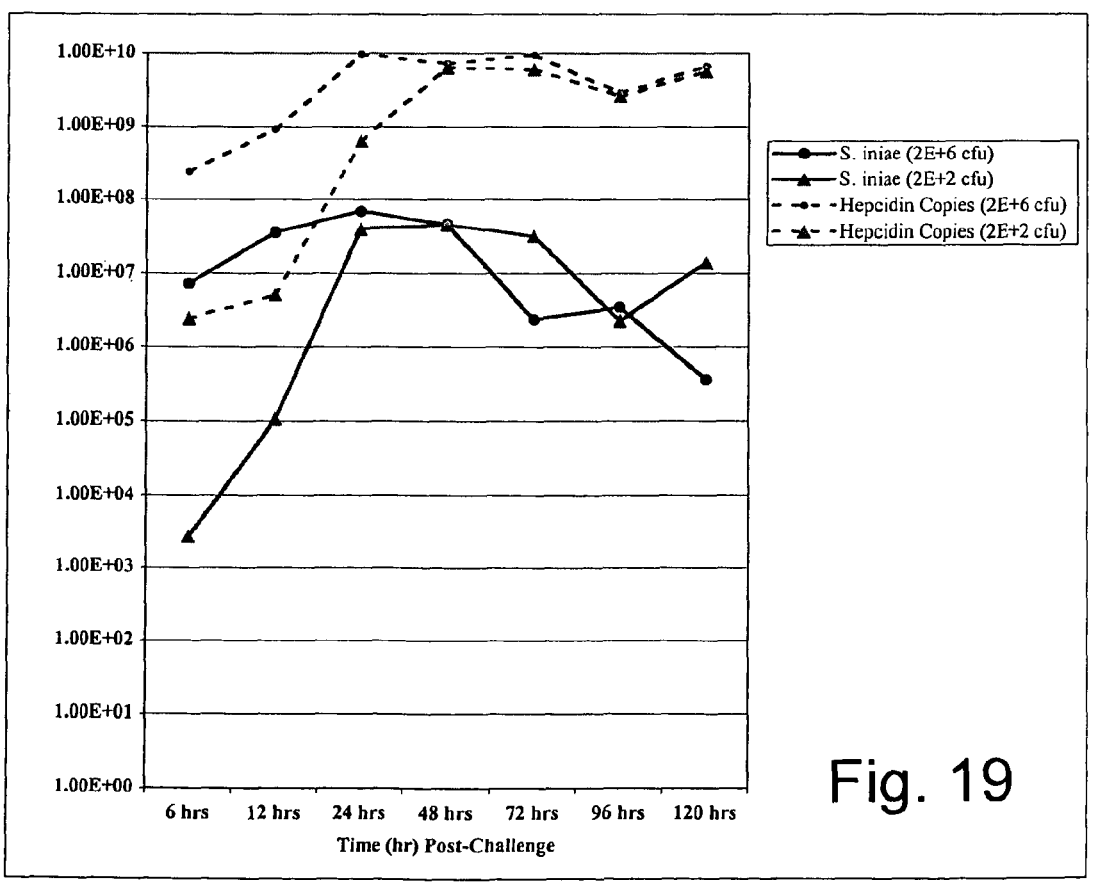
FIG. 19 shows the percent survival over 288 h of HSB induced to produce hepcidin by IP injection of a live-attenuated *S. iniae* mutant.

Upregulation of endogenous hepcidin. Hybrid striped bass (HSB, n=25/group, Ave Wt.=70 g) were injected, interperitoneally (IP), with either a mutant strain of Streptococcus iniae that was attenuated for virulence ('TnM2': ~$2 \times 10^6$ CFU) or with PBS (control group). Both groups were subsequently maintained in 80 1 holding tanks with 26° C. flow-through water; and liver samples from three individual fish from each treatment ('TnM2' and 'PBS') were collected at 24 and 48 hr post-injection to determine relative levels of hepcidin gene expression using sqcRT-PCR (FIG. 19). After 48 hrs, both groups were subsequently challenged (IP), with an LD60 dose of wild-type, virulent Streptococcus iniae ($2 \times 10^4$ CFU), which were then held for an additional 240 hrs in 26° C. flow-through water and monitored for morbidity and mortality.

Figure 20:
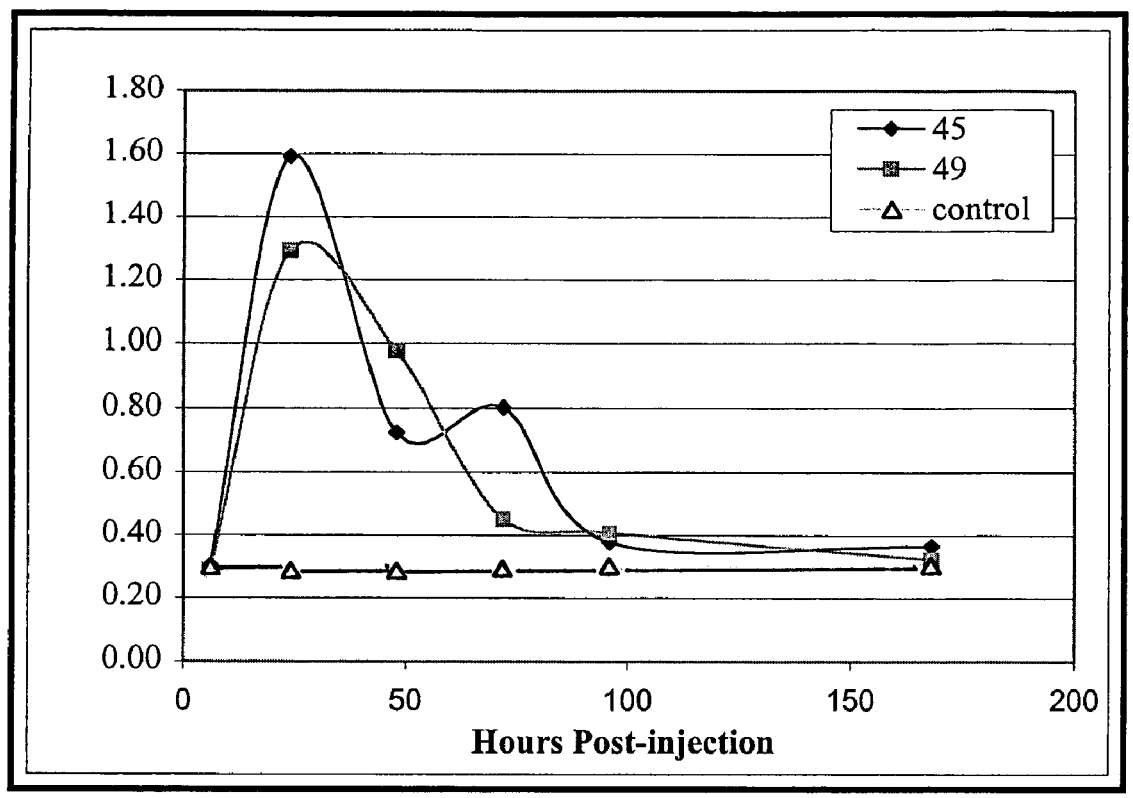
FIG. 20 illustrates graphically the effects of two chitosan compounds on hepcidin in vivo levels in serum of HSB over time.

Screening immunostimulatory compounds using ELISA. One embodiment of the invention contemplates the use of competitive ELISA, and related EIA methods described herein, to screen immunostimulatory compounds for the ability to stimulate with the innate immune systems of vertebrate animals. Immunostimulatory compounds are widely used in vertebrate animal production systems for a preventative treatment against opportunistic diseases and to enhance the general health of animals. For these studies, chitosan, or deacetylated chitin, was used a model immunostimulant. Chitin is known to those practiced in the art to be a major component of fungi and yeast, but also is a major component of crustacean shells. We tested various formulations of chitosan in our fish model system for their immunostimulatory properties were determined by measuring hepcidin levels using competitive ELISA as described above. Two doses of 1 mg and 5 mg injected into HSB fingerlings (30-90 g) in 100 µl volumes of PBS. Three fish per treatment/control were used. The fish were sacrificed 48 h after injection. The levels of mature, bioactive, hepcidin levels in the serum of control and animals receiving the chitosan compounds were determined by competitive ELISA. These preliminary experiments demonstrated two compounds (45 and 49) were investigated further to examine their activities over a one-week time course. In these experiments a dose ten fold greater than the preliminary experiments were used. At each time point, 3 treated fish and 1 control fish for each compound were sacrificed and serum collected. Hepcidin levels in the serum were determined by competitive ELISA and expressed as the inverse of the optical density which is a surrogate measure for hepcidin concentration in a competitive ELISA were high levels of hepcidin are associated with lower optical densities. Thus, the inverse of a low optical density indicates the relatively high levels of serum hepcidin in the sample. Hepcidin levels from fish injected with either 45 or 49 peaked around 24 hours post-injection and returned to basal levels around 96 hours post-injection (FIG. 20). Lipopolysaccharides (LPS) and peptidoglycans are major cell wall components of Gram-negative and Gram-positive bacteria, respectively, and are also associated with immunostimulatory activity. Their effects on serum hepcidin levels can be appreciated by examination of the results (FIG. 19), where a live-attenuated S. iniae mutant, TnM2, caused significant upregulation of hepcidin expression as shown by cRT-PCR analysis (FIG. 19, bottom panel). Further evidence that measurement of hepcidin is useful for screening immunostimulatory activities is shown in Table 2, where HSB vaccinated with an adjuvanted, killed S. iniae vaccine showed significantly higher levels of hepcidin 24 h post-vaccination when compared to controls. It is clear to one practiced in the art, that measurement of mature, folded, bioactive hepcidin using competitive ELISA, or other EIA embodiments of this invention can be applied for screening a wide range of compounds, including probiotics, adjuvants, killed bacterin vaccines, live attenuated vaccines, orally administered vaccines, T-cell epitopes, or feed additives for immunostimulatory activity in vertebrate animals.

Methods for measurement of mature, folded, bioactive hepcidin influids and tissues of vertebrate animals. Key embodiments of the present invention are to provide methods of producing synthetic or recombinantly expressed hepcidin peptides that are folded so that they are identical to the native mature, folded, bioactive vertebrate hepcidins. Hepcidins produced using methods described here are then useful as reagents in measurement of the native, mature, bioactive forms, in animal fluids and tissues. Production of a synthetic version of the native HSB peptide is an object of the present invention, however, several approaches to produce these versions using recombinant technology, are apparent to those practiced in the art. These methods include, but are not restricted to purification of the native form from vertebrate animals, cloning and recombinant expression in plants, bacteria, yeast, mammalian and insect cell lines.

Another embodiment of this invention regards the production of immunoglobulin antibodies that bind specifically to a continuous, discontinuous, or conformation epitope or epitopes of the mature, folded, bioactive forms of vertebrate hepcidins. Development of rabbit polyclonal immunoglobulin antibodies is yet another object of the present invention, although, those practiced in the art can readily appreciate that production of immunoglobulin antibodies can be accomplished in a variety of vertebrate animal, including mouse, rat, hamster, goat, sheep, horse, donkey, chicken, and others. Immunoglobulin antibodies can be produced in these animals using essentially identical methods and reagents as described herein.

Competitive ELISA. Another aspect of the present invention involves using methods described here for the production of mature, folded, bioactive vertebrate hepcidins, in conjunction with methods to produce antibodies to the mature, folded, bioactive vertebrate hepcidins in a competitive ELISA. The competitive ELISA in this invention requires that an antibody specific to the mature, folded, bioactive, vertebrate hepcidin is bound to a solid phase and that remaining binding sites on the solid phase are blocked with non-reactive protein solutions. Following washing of unbound antibody and blocking solutions, the antibodies are challenged with a solution containing a mixture of a known amount of a tracer comprised of the mature, folded, bioactive hepcidin covalently linked to a ligand, and a known volume of the vertebrate fluids or tissues. The solid phase containing the antibody bound to the tracer and native, mature, folded, bioactive form of the vertebrate hepcidin, is washed as before with a buffer, and then exposed to a second binding conjugate containing an enzyme. In some cases the tracer contains the enzyme (e.g. HRP, AP) itself. This method causes a competition for specific antibody binding sites between the tracer and the native, folded, bioactive vertebrate hepcidin, such that once the substrate of the enzyme is added, decrease in signal from the pre-determined level is directly related to the level of the mature, folded, bioactive hepcidin the sample. To one practiced in the art, it is readily apparent that methods described as parts of this invention, can be used to develop a variety of EIA assays, including a sandwich assay, a double sandwich assay, a gel immunodiffusion assay, an agglutination assay, a radioimmunoassay, a precipitin reaction, a fluorescent immunoassay, an immunoelectrophoresis assay, a protein A immunoassay, an immunochromatographic assay, or other EIA assays.

Figure 7A:
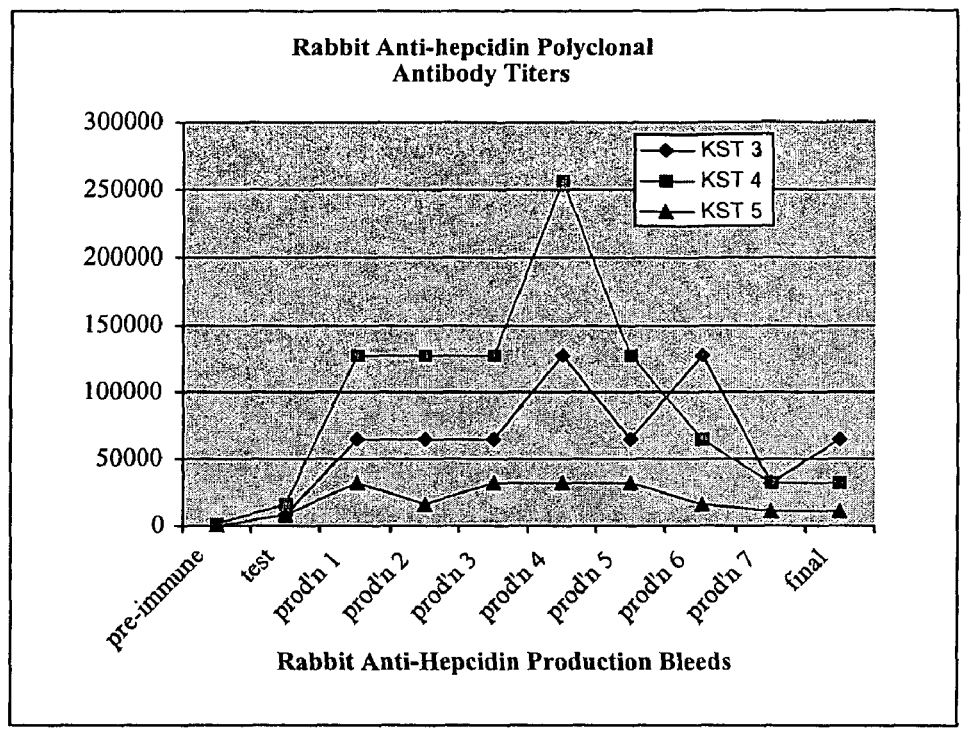
FIG. 7A shows a summary of antibody titers for bass hepcidin.
Figure 7B:
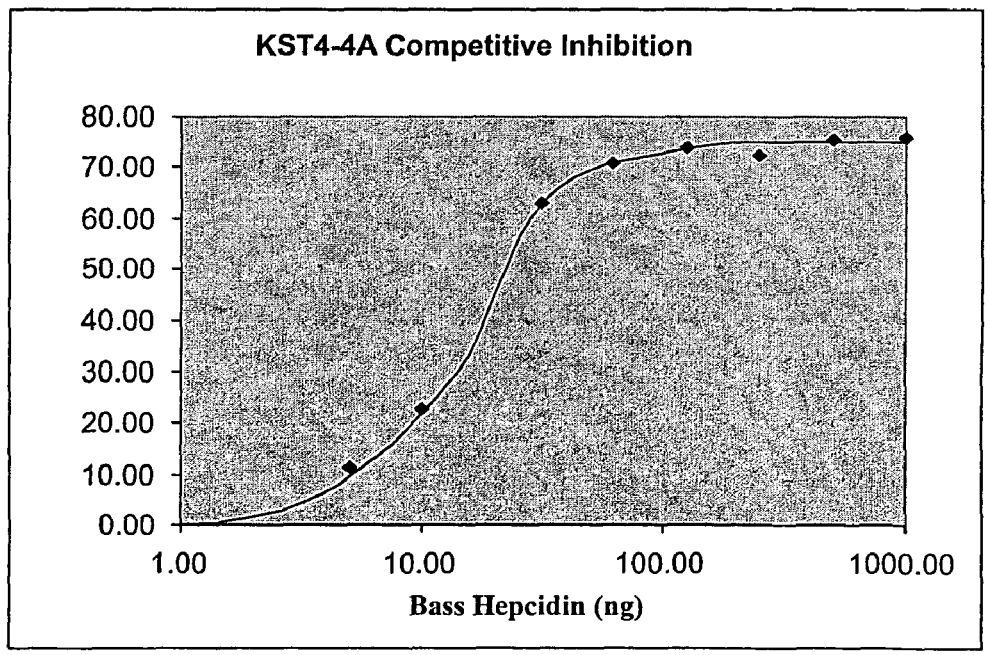
FIG. 7B illustrates an inhibition of an affinity purified antibody using varying amounts of synthetic hepcidin.
Figure 8A:
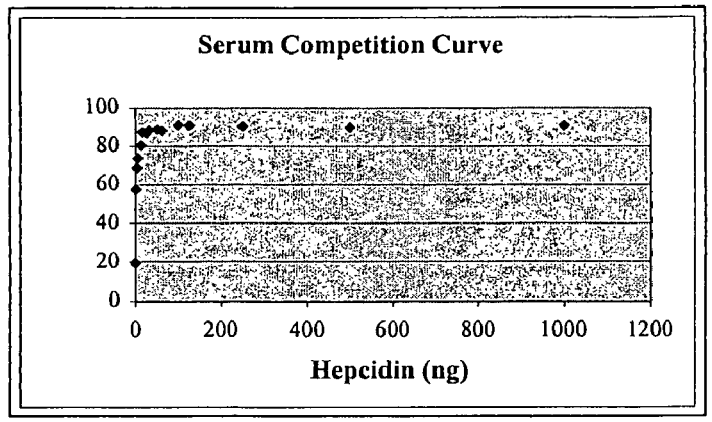
FIG. 8A shows a competition curve of affinity purified anti-hepcidin antibodies with diluted synthetic hepcidin.
Figure 8B:
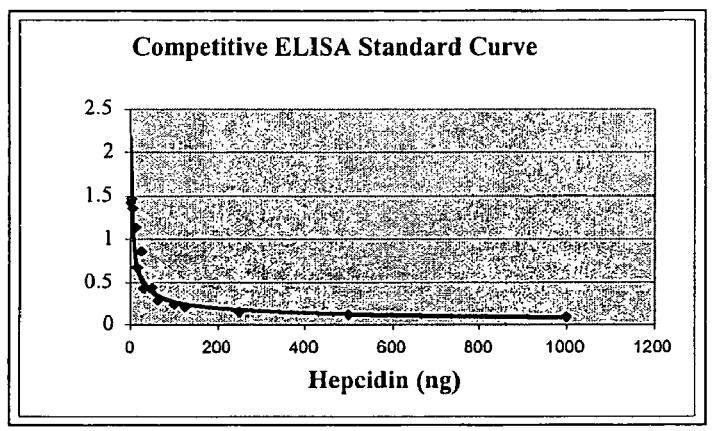
FIG. 8B shows a standard curve generated using an ELISA with biotinylated-hepcidin tracer.
Figure 8C:
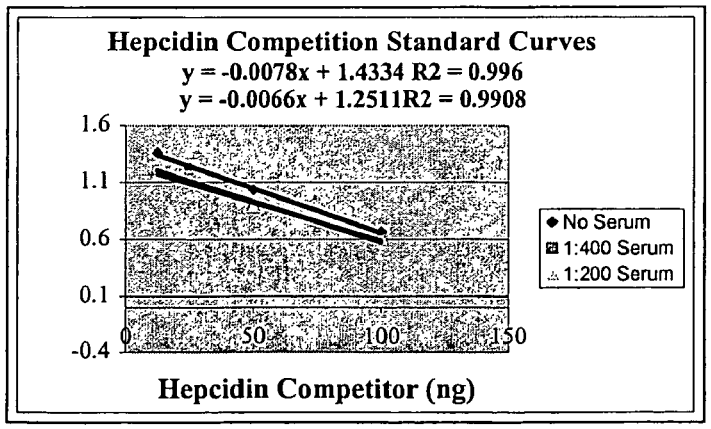
FIG. 8C shows the effects of serum on competitive an ELISA standard curve.
Figure 9:
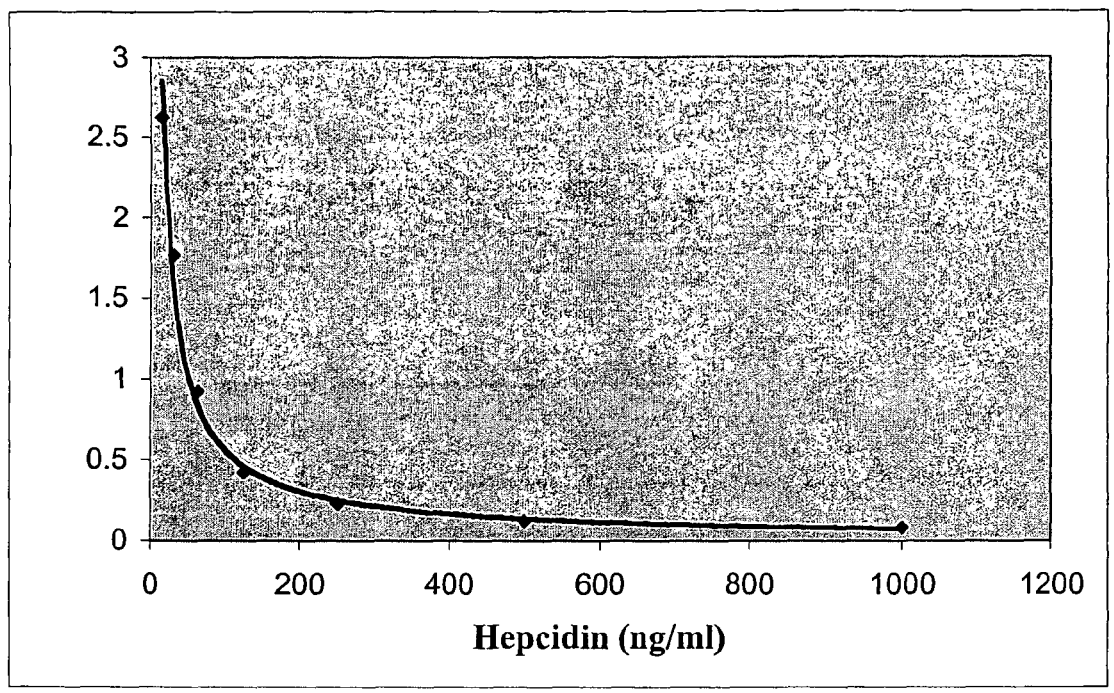
FIG. 9 depicts a sample standard curve for mature bass hepcidin competition ELISA.
Figure 11:
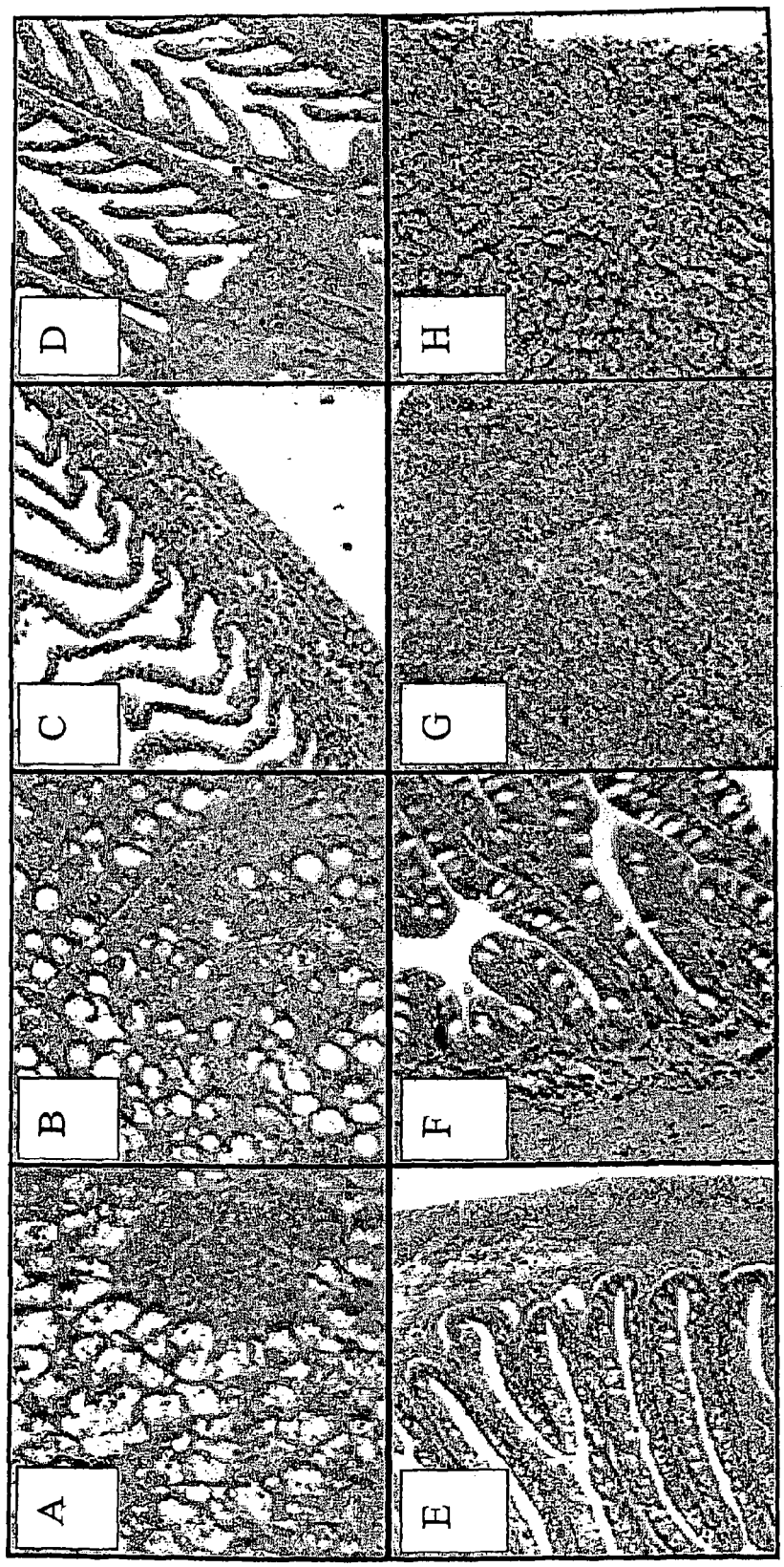
FIG. 11 is a series of micrographs illustrating an immunohistochemistry (IHC) analysis of hepcidin concentrations in liver (A, B) and gill (C, D) in control (A, C) and infected tissues (B, D), as well as IHC analysis of hepcidin concentrations in intestine (E, F) and head kidney (G, H) in control (E, G) and infected tissues (F, H).

Methods for validation of antibodies and conjugates. We collected serum from each of three immunized rabbits (KST3, KST4, KST5). KST3 and 4 are sera from rabbits immunized with hepcidin-KLH conjugates produced using EDC chemistry, while KST5 is sera from conjugates produced using DSS chemistry (FIG. 7A). These data show that KST3 and 4 had the highest titers against the mature, folded, bioactive hepcidin in ELISA. We analyzed the sensitivity by competitive inhibition of the antibodies from each production bleeds from KST3 and 4 by increasing concentrations of hepcidin (data not shown). The inhibition curve shown in FIG. 7B demonstrates that ~75% of the binding of Protein A affinity purified KST4 (1:5000 dilution) is inhibited by 100-1000 ng synthetic hepcidin after a 90 m incubation. 50% inhibition of bass hepcidin specific antibody activity in this experiment was achieved at ~25 ng hepcidin or 2.5 ng/ml. Additional validation of the anti-mature, folded, bioactive hepcidin antibodies described above was performed and their utility in competitive ELISA examined in the presence of varying dilutions of bass serum (FIG. 8 A-C). Note increasing inhibition of signal with increasing amounts of synthetic hepcidin added to tracer. Note the effects of serum on competitive ELISA standard curve (FIG. 8 C) generated with data from (FIG. 8 B) between 10-100 ngs of mature, folded, bioactive hepcidin. Relatively little effect on the standard curve is observed when serum is concentrated or dilute, indicating that non-specific binding of serum proteins is not a significant factor in the competitive ELISA assay. FIG. 9 is an example of a routine standard curve where hepcidin competitor concentrations are expressed as ng/ml, rather than total ngs added to the competition. The competitive ELISA described herein as an embodiment of the present invention, clearly has great utility and has been reduced to practice in our fish farming operations in California were random screening of broodstocks reveals extremely high circulating levels of the mature, native form of hepcidin in infected animals (Table 1 and 2). We have demonstrated the ability of our anti-mature, folded, bioactive hepcidin antibodies to detect native bass hepcidins any tissue examined, including key bodily fluids such as serum, plasma, and urine, as well as key tissues, including liver, gill, intestine, and head kidney (Tables 1, 2; FIG. 11, Micrograh A-H). Urine levels from bass appear to be approximately 10-15 fold lower in concentration of mature, folded, bioactive hepcidin, than serum from the same animals. The ability to detect the mature forms of hepcidin is a critical advantage of this invention in that it permits non-invasive sampling of vertebrate animals for routine monitoring or assessment of diseases.

ELISA Kit. Contents of the kit are:

1 rabbit anti-HSB hepcidin antibody-coated and blocked 96-well strip plate; five 1.0 mL tubes of hepcidin standards (10.0, 5.0, 2.5, 1.0 and 0.0 ug/mL); one 10 mL bottle of biotinlyated hepcidin solution; one packet wash solution (makes 1 L); one packet sample dilution buffer (makes 100 mL); one 15 mL bottle of streptavidin-HRP solution; one 15 mL bottle of TMB substrate; and one 15 mL bottle of $H_2SO_4$ stop solution.

Required supplies are:

pipetters; microplate reader with 450 nm filter; shaker table; refrigerator; distilled water; timer; and paper towels.

The procedure is as follows:

equilibrate plate and all reagents to room temperature; add desired number of strips to 96-well plate frame; add packet of wash buffer to 1 L of distilled water; add packet of sample dilution buffer to 100 mL of distilled water; prepare desired sample dilutions of serum, plasma, or urine in sample dilution buffer; add 50 μl of standard or sample dilution to appropriate wells; add 50 μl of biotinylated hepcidin solution to every well; cover and place on a shaker at 150 rpm at room temperature for 1 hour; briskly discard well contents; wash wells three times with 300 μl wash solution; firmly tap plate on a stack of paper towels to remove residual liquid; add 100 μl of strepavidin-HRP solution to each well; cover and place on a shaker at 150 rpm at room temperature for 30 minutes; briskly discard well contents; wash wells three times with 300 μl wash solution; firmly tap plate on a stack of paper towels to remove residual liquid; add 100 μl of TMB substrate to each well; allow plate to develop for 15 minutes; add 100 μl of stop solution to each well; read the plate at 450 nm with a microplate reader; and fit an appropriate standard curve to the data to determine sample hepcidin concentrations.

Table 1 lists the average serum and urine hepcidin concentrations for three control and three infected bass samples collected from broodstock holding tanks. The control fish were maintained at approximately 22° C. recirculating water systems, all appeared healthy, and there was no history of infection in the control group. The diseased fish were taken from a broodstock tank that had been exhibiting prolonged morbidity and mortality due to stress associated with a prolonged exposure to low temperatures as is commonly observed in *Morone* species.

TABLE 1

| Group | Serum Hepcidin (μg/ml) | Urine Hepcidin (μg/ml) |
| --- | --- | --- |
| Control Fish | 11.16 | 0.99 |
| Infected Fish | 323.50 | 25.84 |

Table 2 shows results from competitive ELISA from HSB serum samples collected from a series of controlled clinical trials, and field production studies at the Kent SeaTech Coachella Valley Production Facility near Palm Springs, Calif., USA. The data from these studies is separated by double lines. The first data set is from a clinical trial where HSB were infected with a dose of virulent *S. iniae* and serum was assayed for hepcidin at the indicated time-points (Rows 1-3). The second data set is from a field study Production Tank 32, where HSB without apparent clinical disease 'Clinically Healthy' and "Infected/Moribund" HSB were sampled and their serum hepcidin levels determined (Rows 4-5). The third data set is a comparison of "Unvaccinated, Control" HSB sampled at time zero, and HSB from the same tank sampled 24 h later (Rows 6-7). The fourth experiment is a clinical where the indicated quantities of synthetic, bioactive, bass hepcidin was injected IP and measured in their serum at the indicated timepoints (Rows 8-11). The HSB in Row 11 received two doses, one at time zero, and the second at 3 h, of the indicated amounts of synthetic hepcidin and were sampled at 6 h only for assessment of serum hepcidin levels. All serum hepcidin levels were determined by the competitive ELISA described herein as an embodiment of the present invention.

TABLE 2

| Sample | n | Range (μg/ml) | Mean (μg/ml) |
| --- | --- | --- | --- |
| S. iniae 15 hr Control | 7 | 5.3-9.1 | 6.87 |
| S. iniae, 15 hr 10^6 CFU | 9 | 19.9-92.0 | 46.87 |
| S. iniae, 72 hr 10^6 CFU | 9 | 2,717-12,828 | 6,318.31 |
| Production T32, Clinically Healthy | 9 | 7.8-8.7 | 8.31 |
| Production T32, Infected/Moribund | 9 | 912-10,327 | 6,927.90 |
| Unvaccinated, Control | 5 | 0.99-1.44 | 1.19 |
| Vaccinated, 24 h Post IP Injection | 5 | 32.5-212 | 82.35 |
| Hepcidin Injection, Control (PBS), 3 h | 9 | 1.1-3.6 | 2.2 |
| Hepcidin Injection, 50 μg, 3 h | 9 | 28.3-49.2 | 39.3 |
| Hepcidin Injection, 300 μg, 3 h | 9 | 102.0-398.8 | 204.3 |
| Hepcidin Injection, 2 × 300 μg, 6 h | 9 | 203.0-263.0 | 229.5 |

Following is a discussion if the immunohistochemical analysis of HSB tissue hepcidin levels following infection.

Liver and Associated Structures. A strong, distinct diffuse signal distribution was observed throughout the hepatocytes of S. iniae-infected fish (FIG. 11, Micrographs A-H). In control tissues (fish injected with PBS), the signal was essentially undetectable. This finding closely parallels that described by others in that the liver is generally accepted as the major site of hepcidin production. One notable difference in the IHC staining pattern of our studies was that the signal was diffuse throughout the hepatocyte (i.e. both apical and basolateral), not restricted to a basolateral distribution as described in U.S. Patent 2004/0096990 (FIG. 11A-B). Since our studies probed tissues with an antibody raised against the mature, refolded, bioactive form of bass hepcidin, this may help explain these apparent differences. A strong, diffuse signal was also observed in the lumen of some of the blood vessels in HSB, probably the result of the antibody reacting with mature peptide being transported into the blood vessels after its hepatocytic production and excretion. This is in contrast with the prior art, where it had been reported that the hepatic vascular system lacked hepcidin reactivity. Also of note was that our findings provide strong evidence that the primary antibody employed ion our studies cross-reacted with a leukocyte-like cell lineage routinely observed within the hepatic blood vessels.

Our present understanding of hepcidin's function as an iron-regulating peptide has focused on the primary role that the liver has played in the production and secretion of this multifunctional peptide. Our molecular and IHC research has demonstrated that not only is the hepcidin gene upregulated in extra-hepatic tissues during bacterial infection but our specific bass hepcidin antibody clearly demonstrates the presence of the mature peptide in many other tissues during episodes of infectious bacterial disease.

Gills and Associated Structures. In gills from control fish that received a PBS injection, a very weak signal was present throughout, usually associated with the amorphous substance present within the blood vessels (FIG. 11, Micrograph C). This observation merely confirms the presence of basal hepcidin levels in an uninfected fish. Occasionally a weak signal was detected within cells located at the base of and along the length of the gill lamellae. While we were unable to differentiate the exact cell type associated with this signal, it was not associated with goblet cells, chloride cells or lamellar epithelial cells (data not shown). Of note was the presence of weak signal associated with the filamental cartilage. In this case some but not all chondrocytes appeared to cross-react with the primary antibody indicating that hepcidin may play a yet undescribed role in chondrocyte proliferation and differentiation. In tissues from S. iniae-infected fish, a strong signal was seen throughout the gills (FIG. 11, Micrograph D). Strong signal was also observed among the amorphous plasma proteins evident within the major blood vessels of the gills (data not shown). In regions of overt inflammation (as evidenced by the presence of increased quantities of many types of inflammatory cells), this intravasculature signal stained even more intensely. Of note was a strong surface-associated signal apparent in a low proportion of the erythrocytes within the central blood vessels of the gill filaments. The biological significance of this observation was not determined however it may be related to iron regulation within specific erythrocytes (or developmental stages thereof) or represent an overabundance of hepcidin and/or its receptor associated with this cell type.

A strong signal was also noted among many of the normal cells present in this organ. Indeed, the most intensely staining regions appeared to reside at the base of and be relatively evenly distributed along the length of the lamellae at fairly constant intervals, suggesting the signal may be associated with a structural cell type (e.g. pillar cells). Often, in the right plane of section, increased signal was associated with cells throughout the basement membrane, adjacent to the central filamental venus sinus. Again cell morphology was difficult to discern, although it appeared to be of leukocyte-like origin. As noted in the control tissues, the antibody to mature bass hepcidin cross reacted with specific chondrocyte nuclei present in the filaments and gill arches.

Intestine and Tissues Associated With the Peritoneum. At 72 hours post infection with S. iniae, a dramatic increase in signal was seen in the columnar epithelium of the intestinal brush border (FIG. 11, Micrograph F). This dramatically increased intestinal signal did not involve the goblet (mucus producing) cells. In contrast, essentially no signal was observed in the corresponding intestinal tissues of fish that were previously injected with PBS (FIG. 11, Micrograph E). These observations strongly support the hypothesis that mature hepcidin may also be produced and post-translationally modified in situ within the columnar epithelium rather than originating from, for example, the lamina propria, and being transported to the brush border. Strong signal was also evident in close association with blood and lymphatic vessels in the smooth muscle of the intestinal tract, particularly proximal to the lamina propria. This observation may support the hypothesis that hepcidin is produced at a distant site (i.e. the liver) and transported to the intestine via a hematogenous route.

The peritoneum of fish experimentally infected with S. iniae contained significant levels of hepcidin, usually associated with the inflammatory cells (mainly macrophages) commonly recruited to this site during inflammation (not shown). This observation was seen both on the serosal surface of the intestinal muscularis as well as throughout the inflammatory foci present within the visceral adipose tissues and mesenteries. Significant signal was also noted among the pancreatic islets distributed throughout the adipose tissue, usually in conjunction with a strong signal associated with the amorphous plasma proteins inside the blood vessels associated with this organ. This observation provides further evidence that the pancreas (rather than the liver) may play a role in regulating hepcidin in an endocrine-like fashion.

Head Kidney and Associated Structures. A strong immunohistochemical signal was observed within the head kidney of fish infected with *S. iniae* (FIG. 11, Micrograph H). In contrast, a similar degree of signal was not detected in the control tissues (FIG. 11, Micrograph G). Based on the signal, it appeared that mature hepcidin was present in close association with the endothelium of the renal portal system, yielding a staining pattern with a reticulated appearance (FIG. 11, Micrograph H). This is a dramatic finding in that while hepcidin was first detected in human urine, this region of the teleost kidney is mainly hematopoetic in function and not excretory as one would expect for an excretory function. When present, signal was also detected within the blood vessels of this hematopoietic organ, usually restricted to specific types of leucocytic cell lineages. Again, a strong hepcidin signal was observed throughout the amorphous plasma proteins seen in the major blood vessels of this organ, suggesting that mature peptide was present in the plasma (not shown).

In the control sections, a weak signal was seen in the chromaffin cells and/or interrenal tissue of the head kidney region but in contrast a strong hepcidin signal was present in the same region of the infected tissues (data not shown). These tissues surround the major blood vessels of the head kidney and although their function is poorly understood, it is felt that they represent the mammalian equivalent of the renal medulla and cortex, respectively. Thus by definition, these teleost tissues represent some form of endocrine function. Thus our findings demonstrate that our antibody to bass hepcidin specifically recognizes epitopes in a tissue of known neuroendocrine origin.

Antimicrobial Spectrum of Activity. Serial dilutions of synthetic hepcidin beginning at 44 μM, were tested in vitro in liquid growth inhibition assays against 21 bacterial strains, a filamentous fungi, and a yeast strain. Table 3 reports a summary of MIC and MBC of bass hepcidin for various microorganisms; the highest concentration tested with bacteria and yeast was 44 μM, while 88 μM was used for the fungi, *A. niger*. The peptide was active against a panel of Gram-negative bacteria including three *E. coli* strains, *Pleisomonas shigelloides*, *Klebsiella pneumoniae*, *Shigella sonnei*, *Shigella flexneri* and *Yersinia enterocolitica*. Hepcidin was not active at 44 μM against another *Klebsiella* sp., *K. oxytoca*, as well as nine other Gram-negative species tested. The minimum inhibitory concentrations of synthetic hepcidin against Gram-negative bacteria ranged from 5.5 to 44 μM, and overall, 8/18 (44%) of the Gram-negative species tested were sensitive to bass hepcidin. The MBCs were either equal to or twice the MIC for all bass hepcidin sensitive strains. Bass hepcidin showed no activity at 44 μM against the three Gram-positive bacteria and single yeast strain tested. Hepcidin displayed anti-fungal activity in vitro against *A. niger* at relatively high concentrations (44 μM). Interestingly, hepcidin was not active against any of the key fish pathogens we tested, including the Gram-positive pathogen, *S. iniae*, and the Gram-negative pathogens, *A. hydrophila*, *A. salmonicida*, and *E. tarda*.

TABLE 3

| Microorganisms | American Type Culture Collection No. | MIC | MBC |
|---|---|---|---|
| Gram-positive bacteria: | | | |
| Entercoccus faecalis (vancomycin-resistant) | 51299 | >44 | Not Tested (NT) |
| Staphylococcus aureus (methicillin-resistant) | 33591 | >44 | NT |
| Streptococcus iniae | Kent Sea Tech Corp. isolates form HSB (KST) | >44 | NT |
| Gram-negative bacteria: | | | |
| Aeromonas hydrophilia | KST | >44 | NT |
| Aeromonas salmonicida | KST | >44 | NT |
| Enterobacter cloacae | 35030 | >44 | NT |
| E. coli | 25922 | 22 | 22 |
| E. coli | 35150 | 22 | 44 |
| E. coli | D31 | 11 | 11 |
| Edwardsiella tarda | KST | >44 | NT |
| Klebsiella oxytoca | 49131 | >44 | NT |
| Klebsiella pneumoniae | 10031 | 22 | 44 |
| Pleisomonas shigelloides | KST | 11 | 22 |
| Pseudomonas aeruginosa | 35032 | >44 | NT |
| Salmonella arizonae | 13314 | >44 | NT |
| Salmonella choleraesuis | 14028 | >44 | NT |
| Salmonella typhimurium | 13311 | >44 | NT |
| Serratia marcescens | 8100 | >44 | NT |
| Shigella flexneri | 12022 | 22 | 44 |
| Shigella sonnei | 9290 | 44 | 44 |
| Yersinia enterocolitica | 23715 | 22 | 22 |
| Filamentous fungi: | | | |
| Aspergillus nigers | | 44 | NT |
| Yeast: | | | |
| Candida albicans | 66027 | >44 | NT |

Figure 12:
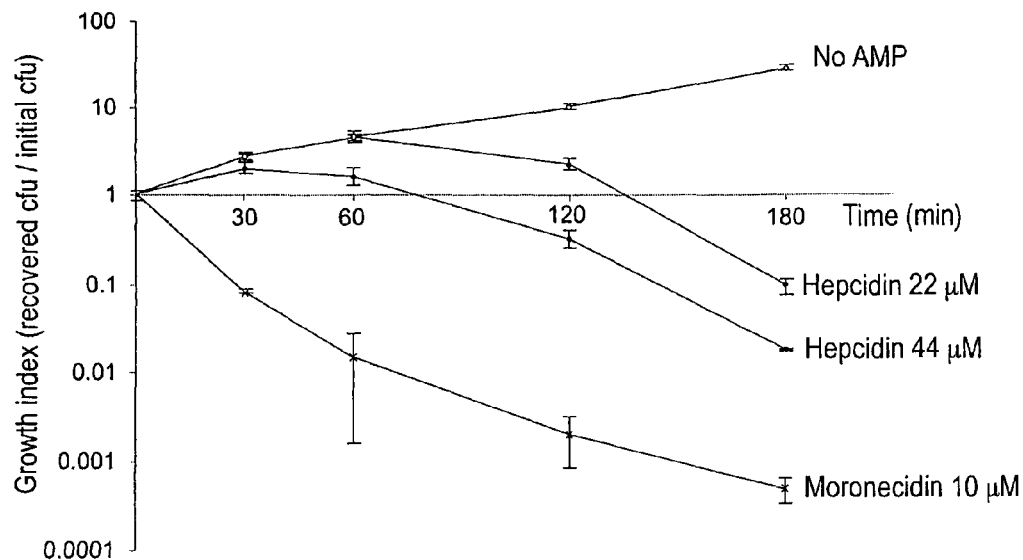
FIG. 12 shows growth index as bacterial CFU recovered/initial inoculum for three experiments employing synthetic bass hepcidin and synthetic moronecidin or water control on a culture of *Yersinia enterocolitica*, with each point representing an average of three experiments.

Microbicidal Kinetics. An experiment was conducted to examine the microbicidal kinetics of bass hepcidin and to compare its killing activity to another bass antimicrobial peptide, moronecidin. Moronecidin is a 22 amino acid, linear, amphipathic α-helical peptide which was originally co-purified from the gill of HSB with hepcidin. These experiments were carried out using *Y. enterocolitica*, where the MIC for hepcidin and moronecidin were measured at 22 μM and μM, respectively. We compared the killing kinetics of hepcidin and moronecidin against *Y enterocolitica* at 30 min intervals over a 3 h time period using 2× their MIC concentrations for this organism (44 and 10 μM; FIG. 12). The bactericidal activities of the peptides were assessed by plating cultures and counting CFUs after overnight incubation at 37° C. Bass moronecidin killed *Y enterocolitica* within minutes of exposure to the bacteria leading to 90% decrease in CFU after 30 min, whereas *Y enterocolitica* cultures were actually growing in the presence of 22 and 44 μM bass hepcidin at this time. Two and half hours were required for a similar 90% reduction of CFU from the original inoculum with hepcidin at 44 μM. The microbiocidal activity of hepcidin was temperature-dependent as was observed for moronecidin.

Figure 13:
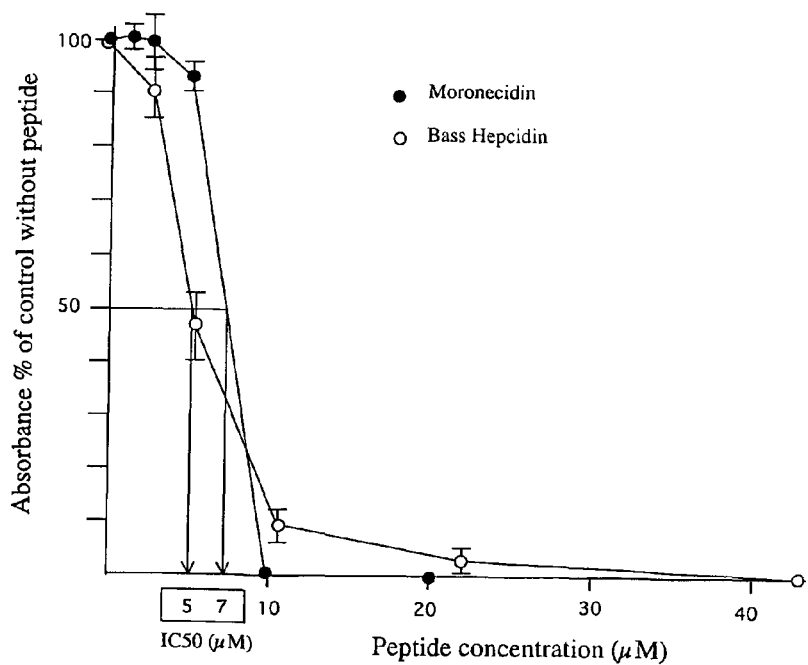
FIG. 13 shows the percentage of absorbance for antimicrobials bass hepcidin (○) and moronecidin (●) when added at different concentrations to spores of *A. niger*, on an average of three experiments.

Fungicidal Activity. A germination assay with spores of the filamentous fungi, *A. niger*, was conducted to test bass hepcidin's fungistatic and fungicidal activities and compare them with those of moronecidin (FIG. 13). No hyphae were observed at a peptide concentration of 44 μM after 2 days incubation at 30° C. At lower concentrations, the peptide caused delayed growth of hyphae with abnormal morphology (data not shown). After 48 hr exposure to the respective peptides, spores were removed and cultured in fresh medium and examined 48 h later for growth. Bass hepcidin was fungistatic at low concentrations with a lower $IC_{50}$ concentration (peptide concentration giving 50% growth inhibition) than moronecidin (5 μM vs. 7 μM) when tested in parallel assays.

Moronecidin, however, was fungicidal at 10 µM, whereas hepcidin was fungicidal at 44 µM (FIG. 13).

Figure 14:
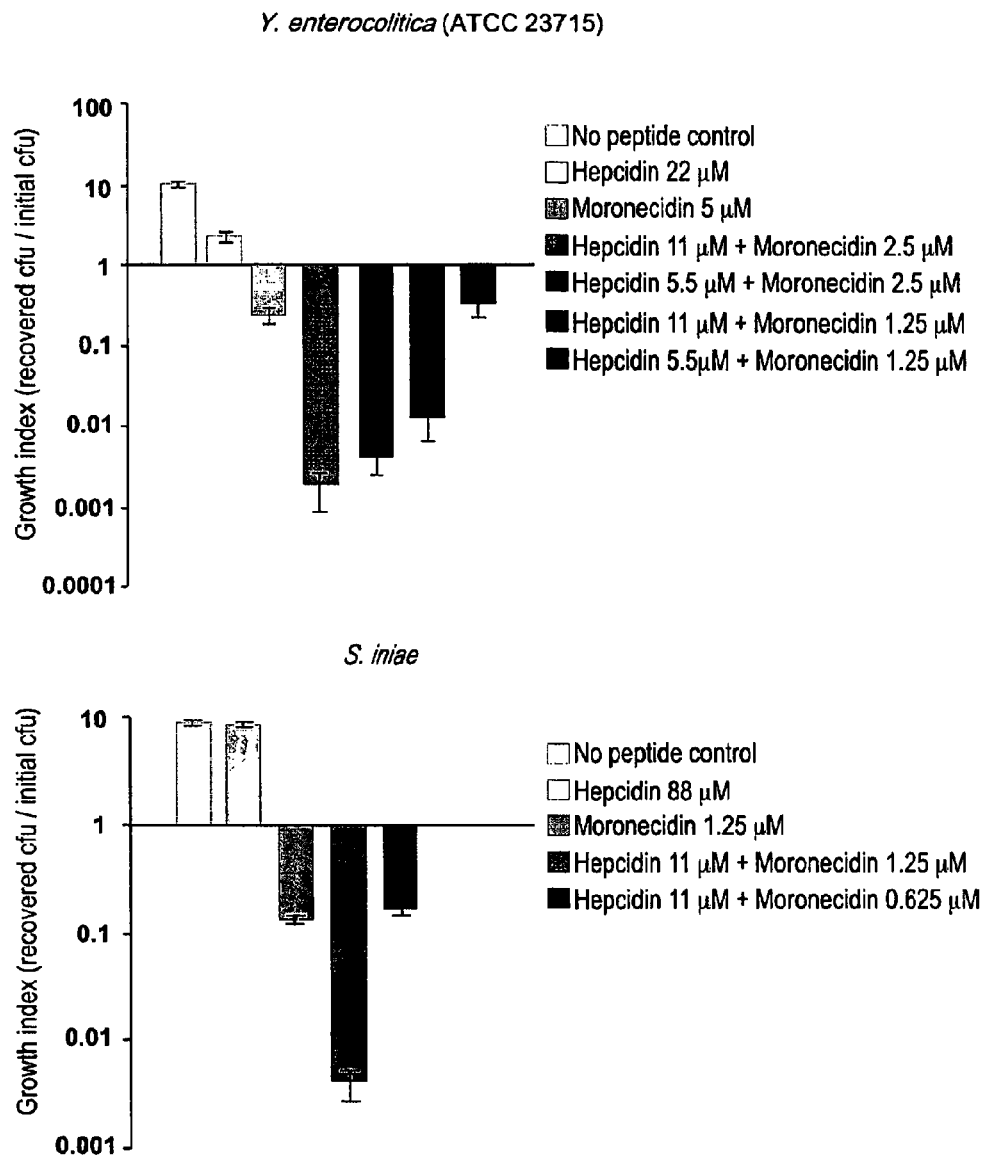
FIG. 14 illustrates the growth index for exponential phase cultures of *Y. enterocolitica* or *S. iniae* with the indicated concentrations of hepcidin, moronecidin or water as a control, and with the experiment performed in triplicate for each sample.

Synergism Between Bass Hepcidin and Moronecidin Antimicrobial Activities. Bass hepcidin and moronecidin were originally co-purified from gill tissues of hybrid striped bass opening the possibility that these peptides are co-localized in this tissue and may act additively or synergistically to kill invading microorganisms. To test for synergism between the two antimicrobial peptides in vitro, we conducted liquid growth inhibition/killing experiments with a Gram-positive (S. iniae) and a Gram-negative bacterium (Y. enterocolitica) using varying concentrations of the two synthetic peptides. The bacteria were cultured in the presence of synthetic bass hepcidin and moronecidin and plated after 2 h incubation at 37° C. for determination of CFU (FIG. 14). We observed (FIG. 14) that two-fold decreases in the MIC of each peptide for Y. enterocolitica, when in combination, reduced CFUs by more than 100 fold below that of either moronecidin or hepcidin alone at their MIC concentrations for this bacteria. A fourfold decrease in the MIC of each peptide in combination yielded similar or better killing of Y. enterocolitica than either peptide alone at their MIC (FIG. 14). Bass hepcidin had no detectable antimicrobial activity against S. iniae after 2 h incubation with concentrations as high as 88 µM (FIG. 14). However, at a hepcidin concentration eight times lower (11 µM), in the presence of 1.25 µM moronecidin, strong killing of S. iniae was observed. Under these conditions, a 10-fold reduction in CFU below that of 1.25 µM moronecidin was observed. While results shown in FIGS. 6A and B give a more intuitive visualization of the synergism between the two peptides, the standard measure for synergism is through calculation of the Fractional Inhibitory Concentration (FIC). We calculated FIC indices against a Gram-positive bacteria (S. iniae) and three Gram-negative bacteria (E. coli, Y. enterocolitica, Shigella sonnei) (Table 4, reporting FIC indices for hepcidin and moronecidin against selected bacteria). An FIC index of 0.5 indicates strong synergy (representing the equivalent of a fourfold decrease in the MIC of each compound tested), while an FIC index of 1.0 indicates that the antimicrobial activity of the two compounds are additive (i.e. a twofold decrease in the MIC of each compound tested). The FIC indices calculated for hepcidin and moronecidin were between 0.5-0.75, indicating strong to moderate antimicrobial synergy between the two peptides.

TABLE 4

| | MIC (µM) | | Lowest FIC index ([A]/[B])[a] |
|---|---|---|---|
| Species | hepcidin | moronecidin | Hepcidin + Moronecidin |
| S. iniae | >88 | 2.5 | 0.56 (11/1.25) |
| E. coli | 22 | 5 | 0.75 (5.5/2.5) |
| Y. enterocolitica | 22 | 5 | 0.50 (5.5/1.25) |
| S. sonnei | 22/44 | 5 | 0.75/0.5 (11/1.25) |

[a]FIC index = [A]/MICA + [B]MICB, where MICA and MICB are the MICs of peptides A and B alone and [A] and [B] are the MICs of peptides A and B in combination. The MICs for the peptides alone are as given in Table II. The numbers in parentheses are the MICs in combination (hepcidin/moronecidin). Since hepcidin MIC against S. iniae is higher than 88 µM, the highest concentration we tested, we chose this value as the hepcidin MIC in the calculation of the FIC index.

Hemolytic Activity. The hemolytic activity of bass hepcidin was tested with erythrocytes from HSB. Bass hepcidin displayed essentially no hemolytic activity towards HSB erythryocytes (Table 5, reporting Hemolytic activity expressed as percent of controls±standard deviation for bass erythrocytes over time.). Greater than 98% of the bass erythrocytes exposed to 44 µM hepcidin for 3 h at 37° C. remained intact. This exposure corresponds to a time point when 96% of Y. enterocolitica exposed to 44 µM hepcidin have been killed (see FIG. 6, Panel A). After 4 h incubation with 44 µM hepcidin, more than 97% of the erythrocytes remained intact. No hemolysis was observed after 4 h at hepcidin concentrations of 11 µM and lower.

TABLE 5

| Hepcidin (µM) | 30 min. | 90 min. | 180 min. | 240 min. |
|---|---|---|---|---|
| 5.5 | 0 | 0 | 0 | |
| 11 | 0 | 0 | 0 | |
| 22 | 0 | 0 | 0.4 ± 0.15 | 0.4 ± 0.4 |
| 44 | 0 | 0 | 1.4 ± 0.3 | 2.5 ± 1.2 |

Figure 15:
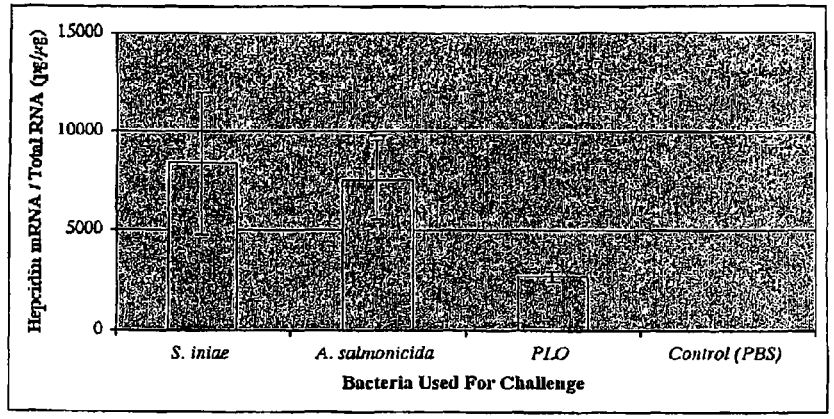
FIG. 15 is a histogram showing quantity of bass hepcidin messenger ribonucleic acid (mRNA) expressed in the liver of HSB fingerlings after infection with *S. iniae, A. salmonicida*, and a *Piscirickettsia*-like organism (PLO).

Clinical trial using cRT-PCR analysis of HSB infected with S. iniae. The mean quantities of hepcidin mRNA per microgram of total RNA expressed in the liver following challenge with S. iniae, and two additional Gram-negative pathogens (A. salmonicida, PLO), are presented in FIG. 15. Results, based on these quantitative competitive RT-PCR assays not only confirm extremely high levels of hepcidin mRNA induction by bacterial challenge with the Gram positive pathogen S. iniae, but also extend these results to phylogenetically distant Gram-negative pathogens (A. salmonicida, PLO). The hepcidin gene was reproducibly induced approximately 30,000-100,000-fold following challenge with all three pathogens. The exact degree by which hepcidin is upregulated in our HSB challenge model/cRT-PCR experimental system is highly dependent on the resting levels of hepcidin expression in livers of healthy HSB fingerlings. In our experiments, we have consistently observed significant competition between the endogenous hepcidin mRNA and 100 femtograms (0.0001 ng; see FIG. 17) of hepcidin cRNA. In fact, the PBS sham-challenged control level of hepcidin mRNA in naive HSB fingerlings was calculated to be 70 femtograms which is near to the limits of detection of the cRT-PCR assay. Determination of resting levels of hepcidin in naïve, healthy HSB will be a critical component of clinical trials performed with vertebrate animals to validate and apply the hepcidin ELISA described within to studies of disease. Interestingly, levels of hepcidin induction in 24-hour liver samples of S. iniae and A. salmonicida-challenged HSB were over two-fold higher than PLO-challenged samples. Lower mean quantities of hepcidin mRNA expression in PLO-challenged HSB may be attributable to a 10-fold lower challenge dose ($3.8 \times 10^4$ CFU) compared to the other two challenge models ($2.0-3.5 \times 10^5$ CFU).

Figure 16:
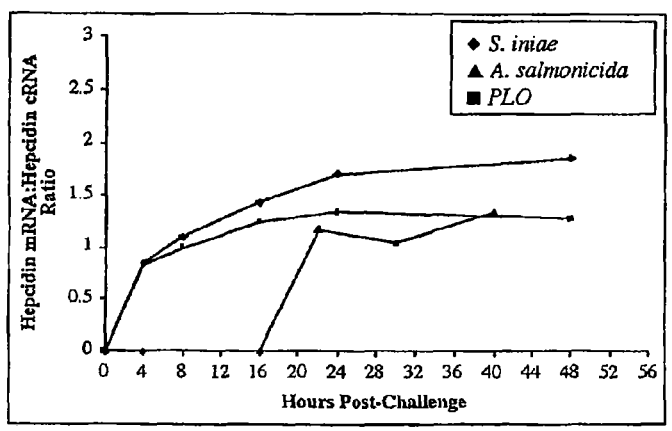
FIG. 16 depicts hepcidin expression levels over time in the liver of HSB infected with *S. iniae, A. salmonicida*, and a PLO.

Temporal analysis of bass hepcidin expression using sqcRT-PCR. Levels of hepcidin gene expression over the first 48 hours post-challenge were evaluated following experimental infections with S. iniae, A. salmoncida, and PLO. In these experiments, 200 ng of total RNA from the livers of six infected individuals at various time points post-challenge (FIG. 16). Hepcidin expression levels over time based on RT-PCR target: competitor signal strength ratios as described above. All three bacterial challenge models in HSB appear to reveal a similar pattern, in which levels of hepcidin gene expression increase maximally over the first 24 hours post-challenge and expression appears to level off between 24 and 48 hours. The consistent and rapid induction of hepcidin mRNA, in response to challenges with a diverse array of bacterial pathogens, lends further support to the use of hepcidin-based assay to detect both Gram-positive and Gram-negative bacterial infections in vertebrate animals.

Figure 17:
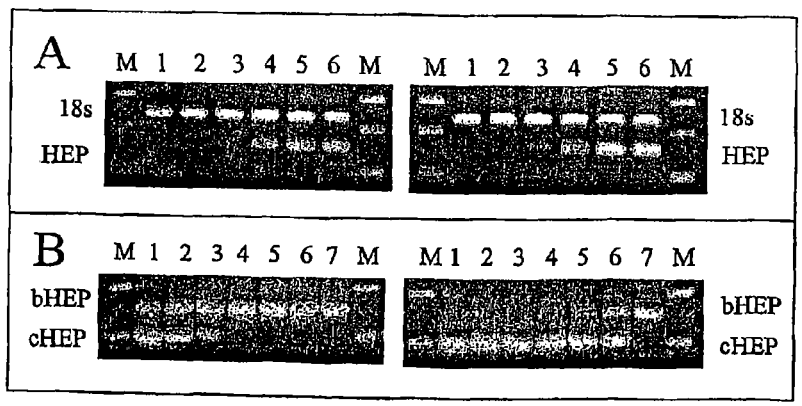
FIG. 17, Panel A shows a representative gel of reverse transcriptase—polymerase chain reaction (RT-PCR) amplicons derived from reactions from a mock-challenged fingerling (Lane 1) and five individual fingerlings sampled postchallenge (Lanes 2-6 respectively) with either *S. iniae* (left image) or *A. salmonicida* (right image), and FIG. 17, Panel B shows gel images of quantitative, competitive RT-PCR amplicons derived using bass hepcidin primers from a *S. iniae* infected bass (left image) and a mock-challenged bass (right image).

Temporal Analysis of Bass Hepcidin Gene Expression Following Bacterial Infection. In a previous study by our group, levels of hepcidin gene expression were assessed at 24 h by kinetic RT-PCR between HSB infected by immersion in a live suspension ($5 \times 10^7$ CFU ml$^{-1}$) of the virulent fish pathogen *S. iniae*, and mock-challenged controls. Those studies demonstrated that hepatic hepcidin expression in bass was strongly upregulated (~4,500-fold) following infection with this Gram-positive bacterium. However, these clinical trials only examined a single pathogen and time point post-infection under conditions that did not allow the pathogen dose received by the HSB to be quantified. To extend this study, we examined hepcidin gene expression at intervals over the first 48 h post-challenge following IP injection of a defined dose of *A. salmonicida* or *S. iniae*. HSB fingerlings infected with either *A. salmonicida* or *S. iniae* exhibited 44% and 78% cumulative mortality, respectively, over the course of seven days. Both pathogens were recovered from the head kidney (*A. salmonicida*) and brain/head kidney (*S. iniae*) of moribund fingerlings, confirming the presence of an active systemic infection. No mortalities occurred in mock-challenged fingerlings and neither pathogen was recovered from the sacrificed control HSB. Differences in hepcidin expression between experimental HSB fingerlings infected with either *A. salmonicida* or *S. iniae* were readily apparent using competitive RT-PCR, especially when comparing hepcidin expression between infected and PBS injected control animals at 24 h (Table 6, reporting hepcidin mRNA expression in bass liver following infectious challenge; for an example of single fish/time point experiment see FIG. 17). Temporal differences in hepcidin expression were also readily apparent following infection with *S. iniae* (FIG. 17).

or Gram-positive (*S. iniae*; $2.4 \times 10^8$ copies ng$^{-1}$ RNA at 48 h) fish pathogens (Table 6; FIG. 17).

Figure 18:
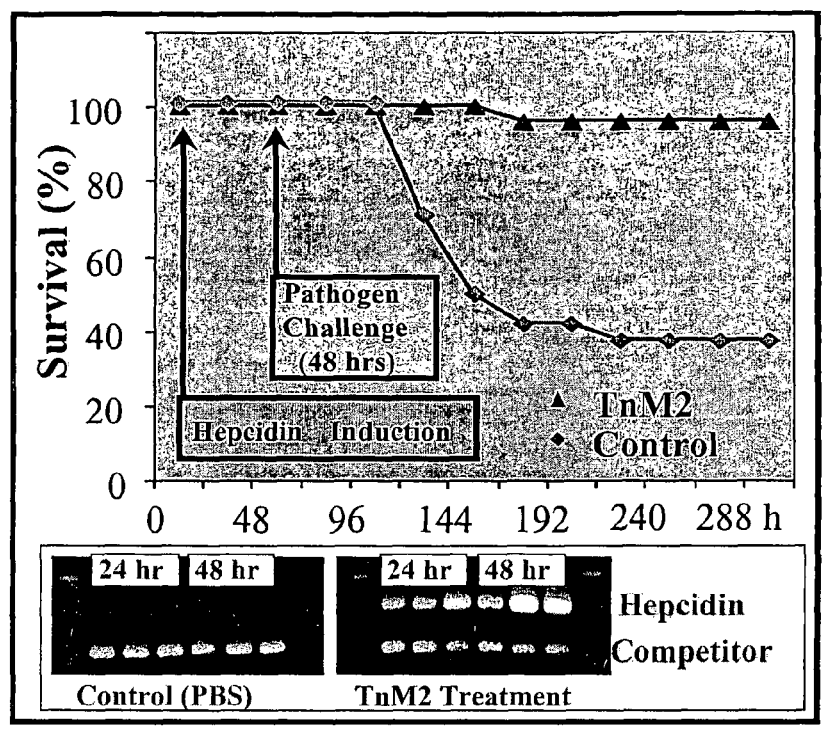
FIG. 18 depicts a hepcidin copy number and spleen levels over time for bass infected with a low dose and a high dose of virulent *S. iniae* bacteria.

Dose response of hepcidin. To evaluate our hepcidin real-time quantitative RT-PCR assay and examine the relationship between hepcidin expression and the degree of infection, we challenged bass (n=30, Ave Wt.=160 g) IP with two doses of the *S. iniae* ($1.98 \times 10^2$ or $1.93 \times 10^6$ CFU) and collected liver tissue from two fish at 0, 6, 12, 24, 48, 72, 96 and 120 h post-challenge for quantification of hepcidin mRNA. Spleen from each fish was homogenized in 20 volumes of sterile PBS, and plated on THB supplemented with 5% sheep blood to estimate *S. iniae* CFUs/gram tissue. Total RNA was isolated from 0.05 grams of liver using TRIZOL™ (MRC). The RNA was quantified, and 1 μg was converted to cDNA in a 20 μl reaction containing 2 μM of d(T)$_{20}$ primer and 200 U SUPERSCRIPT III™ Reverse Transcriptase (Invitrogen). Real-time RT-PCR was performed with 1 μl of the cDNA reaction (~50 ng μl$^{-1}$) in duplicate 25 μl reactions. Duplicate serial dilutions of the hepcidin standard 'pHEP4' (1.0 ng-1.0 fg) were used to generate a standard curve for quantification of hepcidin mRNA. Bass challenged with different doses of *S. iniae* displayed significant differences in CFU/g spleen through 12 hours post-challenge. *S. iniae* levels in the spleen were the same by 24 h and remained elevated through 120 h (FIG. 18). Quantification of hepcidin mRNA in liver tissue samples revealed an expression pattern that was concordant with the pathogen load estimated from spleen tissues. At 12 h, hepcidin expression was significantly lower in HSB challenged with a low dose of *S. iniae*, but the two treatment groups reached similar levels of hepcidin expression by 48 h

TABLE 6

| Hour | Control Copy No.[a] | Range | *A. salmonicida* Mean Copy No. | Range | *S. iniae* Mean Copy No. | Range |
|---|---|---|---|---|---|---|
| 0 | $4.37 \times 10^3$ | $1.27\text{-}7.46 \times 10^3$ | $4.37 \times 10^3$ | $1.27\text{-}7.46 \times 10^3$ | $4.37 \times 10^3$ | $1.27\text{-}7.46 \times 10^3$ |
| 4 | | | $5.23 \times 10^6$ | $5.45 \times 10^5\text{-}9.92 \times 10^6$ | $1.06 \times 10^6$ | $9.78 \times 10^5\text{-}1.14 \times 10^6$ |
| 8 | | | $1.96 \times 10^7$ | $1.54\text{-}2.38 \times 10^7$ | $1.54 \times 10^7$ | $3.73 \times 10^6\text{-}2.72 \times 10^7$ |
| 16 | | | $1.17 \times 10^8$ | $1.02\text{-}1.32 \times 10^8$ | $1.39 \times 10^8$ | $1.16\text{-}1.61 \times 10^8$ |
| 24 | $4.93 \times 10^3$ | $2.39\text{-}7.46 \times 10^3$ | $1.44 \times 10^8$ | $8.9 \times 10^7\text{-}1.99 \times 10^8$ | $1.63 \times 10^8$ | $1.56\text{-}1.70 \times 10^8$ |
| 48 | | | $2.30 \times 10^8$ | $1.66\text{-}2.93 \times 10^8$ | $2.40 \times 10^8$ | $1.89\text{-}2.92 \times 10^8$ |

[a]Copy # is average of two HSB individuals expressed in copies ng$^{-1}$ total liver RNA Hepcidin mRNA copy number was low in the livers of healthy control HSB fingerlings at time zero and at 24 h, comprising approximately $6 \times 10^{-5}$% of total RNA in liver ($4.37\text{-}4.93 \times 10^3$ copies ng$^{-1}$ RNA). Resting levels of hepcidin mRNA in bass liver were approximately 5-7 fg ng$^{-1}$ total RNA. Hepcidin gene expression in HSB was rapidly upregulated following IP challenge with *S. iniae* and *A. salmonicida*, Gram-positive and Gram-negative organisms, respectively. For both fish pathogens, hepcidin expression increased roughly three orders of magnitude between 4 and 8 h, four orders of magnitude by 16 h, and nearly five orders of magnitude by 48 h (Table 6; FIG. 17). Hepcidin hepatic gene expression levels reached >50% and >60% of their 48 h peak levels by 16 h and 24 h, respectively, and continued to increase through the end of the experiment at 48 h. In these clinical trials, hepcidin mRNA comprised approximately 3% of the total liver RNA at 48 h post-infection ($2.3\text{-}2.4 \times 10^8$ copies ng$^{-1}$ total RNA). The rate of increase and overall levels of bass hepcidin mRNA was strikingly similar in HSB fingerlings challenged with similar inoculums of either Gram-negative (*A. salmonicida*; $2.3 \times 10^8$ copies ng$^{-1}$ RNA at 48 h)

post-infection (FIG. 18). These data confirm a dose-dependent response of hepcidin expression to pathogen load, suggesting that our hepcidin-based diagnostics may be able to provide a quantitative measure of the degree of infection. Hepcidin expression increased dramatically (4 to 5 orders of magnitude relative to control levels) upon challenge, and appeared to be maximal by 48 hours. These results are concordant with our previous studies using competitive RT-PCR (cRT-PCR). Hepcidin expression, and bacterial load, remained highly elevated throughout the experiment. Additional experiments, using real-time PCR analysis of hepcidin, are also being conducted to examine the influence of stress on hepcidin expression.

Upregulation of hepcidin in vivo. As part of this invention, we contemplate methods to manipulate endogenous hepcidin expression in vivo in vertebrate animals. To demonstrate that upregulated hepcidin expression is key to or associated with a protective innate immune response, we used a live-attenuated *S. iniae* mutant (TnM2). TnM2 has been shown to be avirulent at doses of $>10^9$ CFU. We predicted that IP injection of $10^6$ CFU of TnM2 would strongly induce endogenous hepatic expression (FIG. 19) and elevate the level of the peptide in blood and other key tissues over several days without causing disease. This experimental model for dietary upregulation of hepcidin allowed us to challenge hepcidin-induced HSB with a virulent strain (K288) and compare their survival with PBS controls where in vivo hepcidin levels are significantly lower. High levels of hepcidin induction (>>0.1 ng/μg RNA) were observed in fish injected with the attenuated *S. iniae* strain, while upregulation of hepcidin in the control group appeared negligible (<<0.1 ng/μg RNA) given the lack of endogenous hepcidin RT-PCR product visualized on the gel. FIG. 19 shows the results of this study and clearly demonstrates that elevated hepcidin is associated with this protective response. At the termination of the experiment, survival in the 'TnM2' treated group, which exhibited high levels of hepcidin expression at 48 hr Oust prior to challenge), was 95.8%. Survival in the untreated control group was only 37.5%. Together, these results clearly indicate that treatments, serving to induce endogenous hepcidin, also confer short-term protection against bacterial pathogens. These results support our concept of using dietary additives to regulate hepcidin levels in vertebrate animals for prevention of diseases, especially those associated with stressful animal production practices.

Antimicrobial Activities. For the methods and inventions described herein, we examined bass hepcidin as a pharmaceutical composition, against 21 species of bacteria including strains previously tested with human hepcidin (Table 3). Consistent with studies of human hepcidin, bass hepcidin was active against *E. coli* but had little or no detectable activities against *P. aeruginosa*, *S. aureus*, or *C. albicans*. Bass hepcidin and human hepcidin were also both active against *A. niger* in spore germination assays (FIG. 13). Our results indicate that bass hepcidin and human hepcidin were both active in a similar range of concentrations against Gram-negative bacteria (Table 3). Bass hepcidin's antimicrobial potency contrasted sharply with another bass AMP, moronecidin, that was also purified from HSB gill tissue (FIG. 12). Moronecidin is a 22 amino acid linear, cationic peptide with an amphipathic, α-helical structure that exhibits a more potent, broader spectrum of bactericidal activity than hepcidin. Peptides like moronecidin are thought to aggregate and interact with negatively charged bacterial membrane components, and disrupt them by forming pores or solubilizing the membrane via a "detergent" effect. This direct membrane disruption is believed to kill the bacterium by creating osmotic imbalance and loss of cytoplasm. Bass hepcidin is cationic and adopts an amphipathic structure in solution, and thus, has the potential to interact with and disrupt bacterial membranes like linear, α-helical peptides. Our studies with *Y enterocolitica* demonstrate that in vitro, hepcidin kills this bacterium much more slowly than does moronecidin (FIG. 12). This indicates inherent biophysical differences between the two peptides. Hepcidin is less cationic and amphipathic than moronecidin. Both of these parameters have been shown to be important structural attributes for potent antimicrobial activity. Alternatively, *Y enterocolitica* is known to have an efflux pump/potassium antiporter to combat the antimicrobial activities of host cationic peptides. Thus, the differences in bactericidal activity between the two peptides indicate different susceptibilities of the peptides to this antibiotic resistance mechanism. Finally, there are indications that hepcidin kills bacteria by a mechanism independent of membrane permeabilization (e.g. inhibiting a key metabolic process), which indicates that prolonged contact with the bacteria is required to exert microbicidal activity.

Hepcidin Expression In Vivo Following Infection. Our results show that infection of bass with either a Gram-positive (*S. iniae*) or Gram-negative (*A. hydrophila*) fish pathogen, induces hepcidin gene expression in the liver with very similar kinetics. The first hepcidin transcripts were detected within hours following experimental infections and expression was maximal at 48 h post infection. The rapidity and remarkable amplitude of this expression profile are consistent with the acute phase response to infections observed in mammals. Human and mice hepcidin expression both require the inflammatory cytokine IL-6, thus defining hepcidin as a type II acute phase response protein. Mice show a four-fold increase in hepcidin expression in response to inflammatory stimulators, while studies in human patients with anemia of inflammation show up to 100-fold greater concentrations of hepcidin in their urine. Despite the limited spectrum and potency of hepcidin antimicrobial activity observed in vitro, there are several possible mechanisms by which hepcidin could be effective in vivo as an antimicrobial compound. We have shown by our methods and competitive ELISA, that serum concentrations of hepcidin reach higher levels than we tested in vitro, compensating for the levels of specific activity observed in vitro. The dramatic upregulation of hepcidin expression in liver and other tissues upon experimental infection of HSB with fish pathogens supports this hypothesis. In this study, bass liver hepcidin expression increased three orders of magnitude within 16 h of infection, four orders of magnitude within 24 h, and was nearly five orders of magnitude above baseline by 48 h post infection (Table 6). The magnitude and duration of the upregulation of hepcidin expression in the liver following infection indicates that high concentrations of hepcidin are important to the innate immune response against these pathogens. Another mechanism by which hepcidin shows to exert strong antimicrobial effects in vivo is through synergistic interactions with other inducible acute phase response proteins, and/or constitutively expressed antimicrobial compounds in the tissues (FIG. 14). There are a number of examples of co-localization of antimicrobial compounds in various tissues and cell types, as well as specific evidence of synergistic activity when AMPs are combined in vitro. Our previous studies have demonstrated that both the hepcidin and moronecidin genes are expressed in the gill tissue of bass and that their mature peptides reside in this tissue. Thus, our demonstration of synergism between hepcidin and moronecidin antimicrobial activities in vitro against both Gram-positive and Gram-negative bacteria reflects an elegant addition to innate immune systems of teleosts. A model where the inducible hepcidin peptide acted synergistically with constitutively expressed AMPs such as moronecidin, indicates an increased broad-spectrum antimicrobial defense during the early stages of an infection.

Hepcidin, Inflammation, and Hypoferremia. In mammals, hepcidin plays a key role in the hypoferremic response during inflammation, and given the similarity of the two structures and activities, there is potential for a similar role for hepcidin in bass and other teleosts. Bacterial pathogens require iron for growth and most have evolved sophisticated mechanisms for obtaining iron from their hosts to support their proliferation. In this regard, hepcidin has been proposed to help combat infection by restricting iron availability to invading pathogens through a strong hypoferremic response, and thus limiting their proliferation. The potential for hepcidin-induced hypoferremia in fish is consistent with studies in trout and salmon, where lower free iron in plasma was observed 24-48 h after injection of LPS. In addition, symptoms of anemia have been observed in bass infected with *S. iniae* or *A. salmonicida*, both of which we have shown to be potent inducers of hepcidin expression.

Strong conservation of the structure and rare vicinal disulfide between bass and human indicates that the hepcidins are functionally constrained from sequence divergence. Since bass hepcidin does not contain any acidic residues, no evidence was found of direct binding of bass hepcidin to ferric iron by NMR. Instead, hepcidin has shown to have the capability of exerting its effects on the innate immune response of teleosts through a combination of activities. The bass model employed in these studies provides a powerful approach to further elucidate hepcidin function(s), including it potential role in hypoferremia in teleosts.

Disease states. One aspect of the present invention is application of methods and reagents produced from those methods to detect disease states in vertebrate animals. For the purposes of the present invention, disease states comprises genetic and non-genetic diseases responsible or associated with iron deficiency, iron overload, and/or changes in iron distribution in tissue such as accumulation of iron in reticuloendothelial cells and decreased serum iron concentration. Disease states also comprise infectious diseases comprises bacterial, fungal, yeast, viruses, encapsulated viruses, prion diseases, and non-specific infectious diseases caused by unculturable organisms; inflammatory disease such as arthritis and certain type of cancer; inherited or non-inherited iron overload diseases; liver diseases; hematological diseases; diseases associated with blood loss, oxidative stress and from exposure to toxic molecules such as heavy metal, carbon monoxide; and neurodegenerative diseases such as Alzheimer's diseases. Due the involvement of bioactive hepcidins with these diseases, the methods to produce the key reagents, and the diagnostic kits for accurate measurement of bioactive hepcidins, are both aspects of the present invention, and enable (i) detection and analysis of hepcidins role in a wide variety of human and other vertebrate animals suffering from, or predisposed to these diseases, and (ii) rapid diagnosis of these diseases. Our diagnostic tool is unique in that the antibodies and associated reagents are all specific to the bioactive form of hepcidin associated with vertebrate iron regulation.

While the invention has been described in connection with the above described examples, it is not intended to limit the scope of the invention to the particular forms set forth, but on the contrary, it is intended to cover such alternatives, modifications, and equivalents as may be included within the scope of the invention. Accordingly, the invention is limited only by the following claims.

What is claimed is:

1. A method for measuring the amount of the hepcidin peptide consisting of SEQ ID NO:28 in a sample of tissue or bodily fluid taken from a human, wherein the measuring comprises use of a competitive Enzyme-Linked Immunosorbent Assay (ELISA), comprising:
   (a) obtaining a sample of a tissue or a bodily fluid from a human, and preparing a solution comprising the sample of the tissue or the bodily fluid;
   (b) providing a known amount of a tracer reagent consisting of:
      (i) the peptide consisting of SEQ ID NO:28 oxidatively folded;
      (ii) a hydrophilic spacer consisting of two (2-(2-Amino-Ethoxy) Ethoxy) Acetic Acid (AEEAc) residues, wherein the peptide of step (b)(i) is covalently linked to the hydrophilic spacer at the amino terminus of the peptide; and
      (iii) biotin covalently linked to the hydrophilic spacer of (b)(ii);
   (c) providing an immobilized antibody that specifically binds to and is specific for the peptide of step (b)(i), and contacting the immobilized antibody with a blocking solution;
   (d) contacting a known amount of the solution of step (a) with a known amount of the reagent of step (b) in the presence of the immobilized antibody of step (c);
   (e) washing unbound tracer reagent from the solution of step (d);
   (f) detecting the amount of tracer reagent of step (b) bound to the antibody of step (c), wherein the detecting comprises use of a competitive Enzyme-Linked Immunosorbent Assay (ELISA); and
   (g) calculating the amount of the peptide consisting of SEQ ID NO:28 in the sample based on results of the detecting of step (f).

2. The method of claim 1, wherein the sample comprises a sample of human blood, plasma, serum, urine, cerebro-spinal fluid (CSF), amniotic fluid, saliva, breast milk, or wound fluid.

3. The method of claim 1, wherein the competitive ELISA comprises use of a microtiter plate, and the immobilized antibody of step (c) is immobilized onto a well of the microtiter plate.

4. The method of claim 1, wherein the level of the peptide consisting of SEQ ID NO:28 in the sample is determined semi-quantitatively or qualitatively.

5. The method of claim 1, further comprising the step of comparing the determined amount of the peptide consisting of SEQ ID NO:28 in a sample obtained from a healthy human or an appropriate control sample with the amount of peptide as consisting of SEQ ID NO:28 in the sample of the tissue or the bodily fluid as calculated in step (g).

6. The method of claim 1, wherein the immobilized antibody of step (c) is an affinity-purified rabbit anti-human hepcidin antibody that specifically binds to the peptide consisting of SEQ ID NO:28.

7. The method of claim 1, wherein the immobilized antibody of step (c) is an affinity-purified mouse, rat, hamster, goat, sheep, horse, donkey or chicken antibody.

8. The method of claim 1, wherein the amount of tracer reagent bound to the immobilized antibody of step (c) is determined using streptavidin-horseradish peroxidase (HRP) and a tetramethylbenzidine (TMB) substrate.

9. The method of claim 1, wherein the competitive ELISA further comprises after step (d) washing the immobilized antibody of step (c) with a buffer, and then exposing the immobilized antibody-tracer reagent and immobilized antibody-sample peptide complexes to a second binding conjugate comprising an enzyme.

10. The method of claim 1, wherein the peptide consisting of SEQ ID NO:28 used in the tracer reagent is an isolated, synthetic or recombinant peptide.

11. The method of claim 1, wherein the peptide of step (b)(i) is made by a method comprising:
(a) solubilizing a recombinant or synthetic peptide consisting of SEQ ID NO:28 in an acetic acid solution to produce a first solution;
(b) diluting the first solution with an aqueous buffer solution containing a chaotropic reagent, an organic alcohol, and an oxidizing reagent to produce a second solution, the organic alcohol enhancing the solubility of the recombinant or synthetic peptide consisting of SEQ ID NO:28, the organic alcohol further preventing precipitation of the peptide during the oxidative refolding, thereby increasing yield;
(c) adjusting the pH of the second solution to a level between approximately 5 and 7; and
(d) exposing the recombinant or synthetic peptide consisting of SEQ ID NO:28 to oxidation for a suitable period of time, thereby causing said peptide consisting of SEQ ID NO:28 to configure to a folded tertiary structure.

12. The method of claim 1, wherein the peptide consisting of SEQ ID NO:28 of step (b)(i) is oxidatively folded before it is covalently linked to the hydrophilic spacer of step (b)(ii).

13. The method of claim 12, wherein the peptide consisting of SEQ ID NO:28 of step (b)(i) is oxidatively folded by a process comprising:
(a) solubilizing the peptide consisting of SEQ ID NO:28 in an acetic acid solution to produce a first solution;
(b) diluting the first solution with an aqueous buffer solution containing a chaotropic reagent, an organic alcohol, and an oxidizing reagent to produce a second solution; and
(c) adjusting the pH of the second solution to a level between approximately 5 and 7.

14. The method of claim 13, wherein: (i) the organic alcohol is approximately 10% isopropyl alcohol; (ii) the pH is adjusted by the addition of ammonium hydroxide; or (iii) the oxidation occurs at room temperature.

15. The method of claim 12, further comprising the purification and screening by high performance liquid chromatography (HPLC) of the oxidatively refolded peptide consisting of SEQ ID NO:28.

16. The method of claim 12, further comprising co-eluting the oxidatively refolded peptide consisting of SEQ ID NO:28 with hepcidin isolated from human urine and conducting HPLC peak analysis.

* * * * *